(12) United States Patent
Cole

(10) Patent No.: US 7,724,367 B2
(45) Date of Patent: May 25, 2010

(54) PARTICLE MONITORS AND METHOD(S) THEREFOR

(75) Inventor: Martin Terence Cole, Braeside (AU)

(73) Assignee: Siemens Schweiz AG, Zuerich (CH)

( * ) Notice: Subject to any disclaimer, the term of this patent is extended or adjusted under 35 U.S.C. 154(b) by 650 days.

(21) Appl. No.: 10/576,642

(22) PCT Filed: Oct. 20, 2004

(86) PCT No.: PCT/AU2004/001435

§ 371 (c)(1),
(2), (4) Date: Apr. 21, 2006

(87) PCT Pub. No.: WO2005/043479

PCT Pub. Date: May 12, 2005

(65) Prior Publication Data

US 2007/0024459 A1   Feb. 1, 2007

(30) Foreign Application Priority Data

Oct. 23, 2003   (AU)   ............................ 2003905839
Nov. 8, 2003   (AU)   ............................ 2003906161

(51) Int. Cl.
G01N 15/02   (2006.01)
(52) U.S. Cl. ..................................... 356/335
(58) Field of Classification Search .......... 356/335–343
See application file for complete search history.

(56) References Cited

U.S. PATENT DOCUMENTS

| | | | |
|---|---|---|---|
| 3,616,410 A | 10/1971 | Shtoffer | 204/195 |
| 3,982,130 A | 9/1976 | Trumble | 250/373 |
| 4,099,065 A | 7/1978 | Malinowski | |
| 4,181,439 A | 1/1980 | Tresch et al. | 356/338 |
| 4,288,790 A | 9/1981 | Schnell | 340/628 |
| 4,379,290 A | 4/1983 | Muggli et al. | 340/629 |

(Continued)

FOREIGN PATENT DOCUMENTS

AU   573243   6/1988

(Continued)

OTHER PUBLICATIONS

D. S. Goodman, "Method for Localizing Light-Scattered Particles," IBM Technical Disclosure Bulletin, vol. 27, No. 5, Oct. 1984, pp. 3164.

(Continued)

*Primary Examiner*—Michael P Stafira
(74) *Attorney, Agent, or Firm*—Laurence A. Greenberg; Werner H. Stemer; Ralph E. Locher

(57) ABSTRACT

The present invention relates to the field of the detection, analysis and/or determination of matter or particles suspended in fluid. In one particular form, the present invention relates to smoke detectors, which detect unwanted pyrolysis or combustion of material. In another form, the present invention relates to smoke detectors of the early detection type, and which may be applied to ventilation, air-conditioning or duct monitoring of a particular area. In yet another form, the present invention relates to surveillance monitoring, such as building, fire or security monitoring. in still another form, the present invention relates to environment monitoring, such as monitoring, detection and/or analysis of a fluid, zone, area and/or ambient environment, including commercial and Industrial environments.

16 Claims, 18 Drawing Sheets

U.S. PATENT DOCUMENTS

| | | | |
|---|---|---|---|
| 4,426,640 A | 1/1984 | Becconsall et al. | 340/632 |
| 4,457,624 A * | 7/1984 | Goldberg et al. | 356/336 |
| 4,564,762 A | 1/1986 | Doherty et al. | |
| 4,679,939 A * | 7/1987 | Curry et al. | 356/336 |
| 4,781,065 A | 11/1988 | Cole | |
| 4,854,705 A | 8/1989 | Bachalo | 356/336 |
| 4,906,978 A | 3/1990 | Best et al. | 340/630 |
| 5,104,221 A | 4/1992 | Bott et al. | 356/336 |
| 5,372,477 A | 12/1994 | Cole | 415/218.1 |
| 5,440,145 A | 8/1995 | Cole | 250/574 |
| 5,502,434 A | 3/1996 | Minowa et al. | 340/630 |
| 5,529,107 A | 6/1996 | Iwamura | |
| 5,576,697 A | 11/1996 | Nagashima et al. | 360/630 |
| 5,665,925 A | 9/1997 | Gerteis | 73/865 |
| 5,755,250 A | 5/1998 | Cole | 137/78.5 |
| 5,841,534 A | 11/1998 | Lorenz | 356/336 |
| 6,184,537 B1 | 2/2001 | Knox et al. | 250/574 |
| 6,414,746 B1 | 7/2002 | Stettner et al. | 356/4.01 |
| 7,057,712 B2 * | 6/2006 | Beck et al. | 356/72 |
| 7,075,445 B2 * | 7/2006 | Booth et al. | 340/630 |
| 7,075,646 B2 | 7/2006 | Cole | |
| 2002/0084907 A1 | 7/2002 | Rattman et al. | |
| 2002/0101345 A1 | 8/2002 | Pattok et al. | 340/516 |
| 2003/0011770 A1 | 1/2003 | Cole | |

FOREIGN PATENT DOCUMENTS

| | | |
|---|---|---|
| AU | 573594 | 6/1988 |
| AU | 575845 | 8/1988 |
| AU | 576361 | 8/1988 |
| AU | 577538 | 9/1988 |
| AU | 577551 | 9/1988 |
| AU | 80708/91 | 1/1992 |
| AU | 27746/92 | 5/1993 |
| AU | 40503/93 | 12/1993 |
| AU | 40504/93 | 12/1993 |
| AU | 663758 | 10/1995 |
| EP | 0 076 338 | 4/1983 |
| EP | 0 462 642 | 12/1991 |
| EP | 0 463 795 | 1/1992 |
| GB | 1 527 965 | 10/1978 |
| GB | 2 193 570 | 2/1988 |
| GB | 2193570 | 2/1988 |
| GB | 2 267 963 | 12/1993 |
| GB | 2267963 | 12/1993 |
| GB | 2 273 769 | 6/1994 |
| GB | 2273769 | 6/1994 |
| GB | 2 319 604 | 5/1998 |
| GB | 2 319 605 | 5/1998 |
| GB | 2319604 | 5/1998 |
| GB | 2319605 A | 5/1998 |
| WO | WO 00/07161 | 2/2000 |
| WO | WO 01/59737 | 8/2001 |
| WO | 2005043479 A1 | 5/2005 |

OTHER PUBLICATIONS

European Search Report for European Patent Application No. 01 903 514.6, Mar. 17, 2006.

* cited by examiner

PARTICLE MONITORS AND METHOD(S) THEREFOR

FIELD OF INVENTION

The present invention relates to the field of the detection, analysis and/or determination of matter or particles suspended in fluid.

In one particular form, the present invention relates to smoke detectors, which detect unwanted pyrolysis or combustion of material. In another form, the present invention relates to smoke detectors of the early detection type, and which may be applied to ventilation, air-conditioning or duct monitoring of a particular area. In yet another form, the present invention relates to surveillance monitoring, such as building, fire or security monitoring. In still another form, the present invention relates to environment monitoring, such as monitoring, detection and/or analysis of a fluid, zone, area and/or ambient environment, including commercial and industrial environments.

As will become apparent, the present invention has broad application and thus the particular forms noted above are only given by way of example, and the scope of the present invention should not be limited to only these forms.

BACKGROUND ART

The present inventor has determined an understanding that the type of smoke produced in various pyrolysis and combustion circumstances is different. Fast flaming fires tend to produce a very large number of very small solid particles which may agglomerate into random shapes to form soot. In contrast, the early stages of pyrolysis tend to produce a much smaller number of relatively large liquid particles (of high boiling point), typically existing as aerosols that may agglomerate to form a larger, translucent spheres.

The present inventor has also determined an understanding that the detection of relatively large particles which slowly increase in quantity over an extended period of time would typically indicate a pyrolysis or smouldering condition, whereas the detection of numerous small particles arising quickly and without earlier pyrolysis or smouldering could indicate arson involving the use of accelerants.

The present inventor has also determined an understanding that dust particles are generated by the abrasion or non-thermal decomposition of natural materials or organisms in the environment and that such particles are in general very large compared with smoke particles.

The present inventor has also determined an understanding of the following:

Conventional point type smoke detectors are primarily designed for ceiling installation in a protected area. These detectors have relatively low sensitivity and have difficulty in detecting the presence of unwanted pyrolysis where large volumes of air pass through the area being monitored, thus diluting the ability for the detector to sense the presence of unwanted pyrolysis.

To overcome these disadvantages, highly-sensitive aspirated smoke detectors where developed, and are often deployed on ducts for the purpose of monitoring an area. These detectors provide a measure of sensitivity some hundred times greater than convention point detectors. These aspirated systems employ suction pressure via an air pump and also employ a dust filter to reduce unwanted dust pollution from soiling the detector or from being detected indistinguishably from smoke and causing the triggering of a false alarm.

The smoke detector preferably employed in an aspirated system is a nephelometer. This is a detector sensitive to many sizes of particles, such as the many smoke particles produced in fires or during the early stages of overheating, pyrolysis or smouldering.

Optical type smoke (or airborne particle) detectors of the prior art typically use a single light source to illuminate a detection zone that may contain such particles. The use of two light sources has been proposed for some detectors. A proportion of this light may be scattered off the particles toward a one or more receiver cells (or sensors). The output signal(s) from the receiver cell(s) is used to trigger an alarm signal.

Other detectors use a laser beam, providing a polarised monochromatic light source, typically in the near infrared wavelength. These detectors, however, are not considered to be true nephelometers as they are prone to being overly sensitive to a particular particle size range at the expense of other size ranges.

The disadvantage suffered by the above detectors is their relative insensitivity to very small particles characteristic of early pyrolysis and incipient fires, as well as certain fast flaming fires.

Ionisation smoke detectors, on the other hand, utilise a radioactive element such as Americium, to ionise the air within the detection chamber. These detectors are relatively sensitive to very small particles produced in flaming fires, but relatively insensitive to larger particles produced. In pyrolysis or smouldering. They have also been found relatively prone to draughts, which serve to displace the ionised air within the detection chamber and thus trigger a false alarm. This places a practical limit on their useful sensitivity.

Other smoke detectors have used a Xenon lamp as a single light source. The Xenon lamp produces a continuous spectrum of light similar to sunlight, embracing ultraviolet, visible and infrared wavelengths. Use of this light source can detect all sizes of particles and the detectors produce a signal that is proportional to the mass density of the smoke, which is characteristic of a true nephelometer. However, the type of fire cannot be characterised because the particular particle size cannot be discerned. The Xenon light also has only a relatively short life-span of some 4 years and its light intensity is known to vary, which affects the sensitivity.

The present inventor has also realised that in order to provide a wide output range in sensitivity, prior art detectors provide an analog to digital converter (ADC) used to apply the smoke level data to a microprocessor. With careful design, substantially all of the capacity of the ADC is used to represent the maximum smoke level, such as (typically) 20%/m. ADC's operating at 8-bit resolution are useful, whereas a 10 bit or larger ADC's are more expensive and require larger microprocessors, A 10-bit ADC has been found to allow this 20%/m level to be divided into 1024 steps, each step representing an increment of 20/1024=0.02%/m. So the steps are 0, 0.02, 0.04, 0.06, etc, with no opportunity for finer increments. At low smoke levels this is considered a very coarse resolution, making it difficult to set alarm thresholds finely. However at high smoke levels, a resolution of 0.02%/m is unnecessary—the ability to set an alarm threshold at 10.00%/m or 10.02%/m for example, has little if any benefit. So the resolution of the prior art detectors is considered too coarse at low smoke levels and too fine at high smoke levels.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

An object of the present invention is to provide a particle detection apparatus and method(s) which enable an improved detection, discrimination and/or analysis of particles, pyrolysis, smouldering and/or flaming events and dust, thus providing a corresponding improvement in fluid-borne particle detection.

A further object of the present invention is to provide a particle detection apparatus and method(s) suitable for use with ducts or as a stand-alone detector and/or monitor.

A still further object of the present invention is to alleviate at least one disadvantage associated with the prior art.

SUMMARY OF INVENTION

In accordance with aspects of the present invention, the monitoring, surveillance, determination, detection and/or analysis of particles, environment, fluid, smoke, zone or area may comprise determination of the presence and/or characteristic(s) of the particles as is required given the particular application of the present invention.

In this regard, an aspect of invention provides, a method of and device for determining, in a fluid sample, the presence of particle(s) having substantially a predetermined size or range of size(s), the method comprising the steps of illuminating the sample with a first wavelength of light, obtaining a first response signal indicative of the first illumination, illuminating the sample with a second wavelength of light, obtaining a second response signal indicative of the second illumination, and determining the presence of the particles having the size or range of size(s) by comparing the first and second signals.

Preferably, the illuminations are horizontally and/or vertically polarised.

In another aspect of invention, there is provided a gain control apparatus adapted for providing gain control in a particle monitor, said apparatus comprising a first gain stage having a first amplifier, a second gain stage having a second amplifier, and a voltage or current-controlled feedback from the output of the second stage to the input of the first stage so that the frequency response of the amplifier is unaffected by said feedback.

In still another aspect of invention, there is provided a method of determining a service interval for a particle monitor, the method comprising the steps of determining the presence of dust particle(s), providing a measure of the presence of the particle(s), and providing a service indication when the measure has reached a predetermined threshold.

In yet another aspect of the invention, there is provided a particle monitor chamber, comprising a first lens operable in association with a source of illumination, a second lens adapted to focus impinging light toward a receiver cell, and a primary iris configured to substantially prevent light emanating directly from the first lens to impinge on the second lens.

In a further aspect of the invention, there is provided a method of and device for determining the velocity of fluid flowing through a given area, the method comprising the steps of providing a first sensor in the path of the fluid flow at a point of relatively, low fluid velocity, providing a second sensor in the path of the fluid flow at a point of relatively higher fluid velocity, the second sensor having substantially similar temperature characteristics as the first sensor, and determining the fluid velocity based on a measure of the cooling effect of the fluid passing the first and second sensors.

Additionally, there is provided in accordance with another aspect of invention, a method of and device for mounting a housing on a duct, the method comprising the steps of providing at least one tab element in association with the housing, locating the housing proximate the mounting area of the duct, shaping the tab element to substantially fit a profile of the duct proximate the mounting area, and attaching the housing using the tab element.

The present invention also provides a monitor for monitoring the presence, concentration and characteristics of particulates in fluid medium.

The present invention also provides, as an output triggering the threshold or alarm of the detector, a logarithmic signal. This means a signal, the amplitude of which may be compressed according to a logarithmic function or scale. The logarithmic signal may represent various attributes of particles detected, such as the presence, number, frequency, concentration and/or duration.

In essence, in one aspect of invention, different wavelengths, various ranges of wavelengths and/or polarisation are used to detect predetermined particles in fluid.

In essence, in another aspect of invention, subtraction or providing a ratio of two signals enables a more measurable output indicating the detection of particles and the particle sizes.

In essence, in another aspect of invention, this output indicating the detection of particles is amplified in accordance with the two signals.

Other aspects and preferred aspects are disclosed in the specification and/or defined in the appended claims, forming a part of the description of the invention.

The present invention has been found to result in a number of advantages, such as reduced size, cost and energy consumption while achieving the highest industry standards for sensitivity, reliability, maintenance period and false alarm minimisation, and/or monitoring of an environment for the presence of smoke and/or dust particles such that very high sensitivity to smoke may be provided without suffering false alarms due to dust.

Throughout this specification, reference is made to a number of different light sources having certain wavelengths. Reference to the light sources and wavelengths is made only as they are current commercially available light sources. It is to be understood that the principles underlying the present invention have equal applicability to light sources of different wavelength(s).

A monitor may include reference to a detector or similar apparatus.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, and in which.

DETAILED DESCRIPTION

In the embodiment described, at least two channels are referred to, one being channel A, which uses wavelengths such as red or infrared wavelengths, the other being channel B, which uses wavelengths such as blue wavelengths. Additional channels could be employed such as channel C, which uses wavelengths such as green wavelengths. Other wavelengths may also be employed in accordance with the present invention, as will become apparent in the following description. Generally, it is preferred if a reading established from a longer wavelength is compared with a reading establish from a shorter wavelength. Most preferably, the longer wavelength is subtracted from the shorter wavelength. A ratio may also be used to compare wavelength readings.

Wavelengths of Light

In one aspect of invention, it has been determined by the present inventor that the wavelengths of light employed have an important bearing on the sensitivity of the present device to particle sizes. The scattering of light from particles over various size ranges has been described in 'Absorption and Scattering of Light by Small Particles' by Bohren C F and Huffman D R, ISBN 0-471-05772-X.

It has been determined that Mie equations are appropriate for considering particles of a size range appropriate to common smoke and dust. Fast flaming fires tend to produce a very large number of very small carbonaceous particles which may agglomerate into random shapes to form soot. In contrast, the early stages of pyrolysis tend to produce a much smaller number of relatively larger liquid particles (of high bolting point), typically existing as aerosols that may agglomerate to form even larger, translucent spheres or droplets. Dust particles generally result from mechanical abrasion and have random shapes that can be approximated as yet larger spheres for modelling purposes. A source of smoke or dust is unlikely to be mono-disperse (contain one particle size), but is more-likely poly-disperse, with a size range that may follow a Gaussian distribution. It has been found by the inventor that a typical standard deviation for the size distribution is in the vicinity of 1.8 to 2.

It has also been found that airborne particle distributions in cites are bimodal, peaking at around 0.1 micron and 10 micron. Typically, smoke particles lie in the range 0.01 to 1 micron, whereas airborne dust particles lie in the range 1 to 100 micron. However there is some overlap at the 1 micron boundary because the smallest dust particles in nature are smaller than the largest possible smoke particles.

The present inventor has also determined that certain particle sizes are more easily discerned by particular (different) wavelengths of light. Given this, we use two wavelengths of incident light. The light can range anywhere from blue to red (and infrared). An example is light ranging from 400 nm (blue) to 1050 nm (red). For example, 430 nm (blue) and 660 nm (red) could be used.

Figure 1:
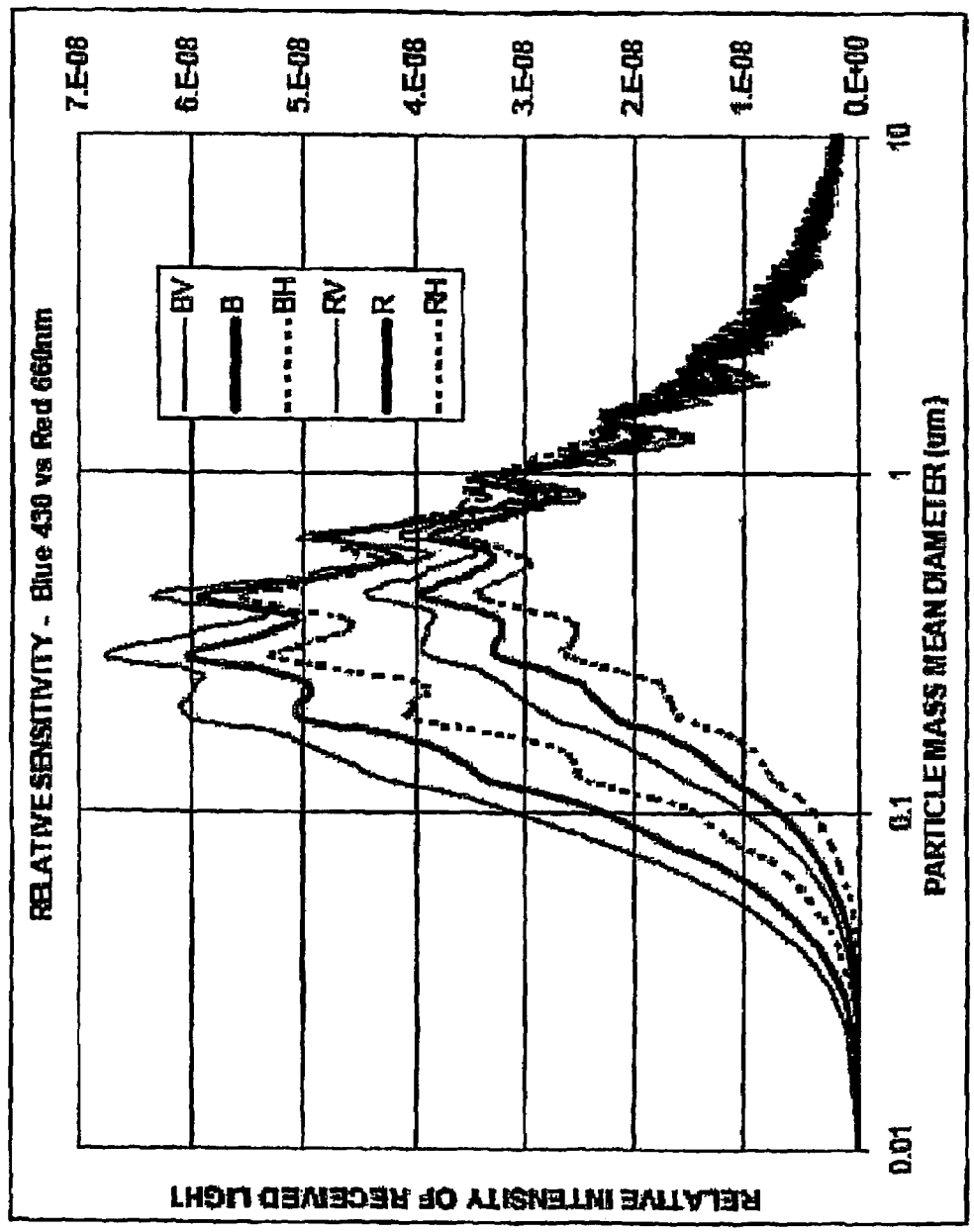
FIG. 1 illustrates results of blue 430 nm and red 660 nm wavelengths to particles over a range of particle sizes.

By application of Mie theory to particle sizes ranging from 0.01 to 10 micron mass mean diameter and using a standard deviation of 1.8, FIG. 1 shows the results for two wavelengths of incident light, 430 nm (blue) and 660 nm (red), each being unpolarised, vertically polarised or horizontally polarised and projected at the same angle relative to the optical axis.

In FIG. 1, the blue family of results (B Blue unpolarised, BV=Blue Vertically polarised, BH=Blue Horizontally polarised) are quite suitable for the detection of smoke and dust, whereas the red family of results (R, RV and RH) are equally suitable for the detection of dust but are comparatively poor at detecting a wide range of smoke particles due to the lack of response to small particles. All of the graphs of FIG. 1 come together above about 0.8 micron whereas there is a significant difference between the graphs for particle sizes smaller than this. The best separation is achieved for blue-vertical (BV) vs red-horizontal (RH). The graphs cannot be effectively separated at larger diameters. The periodicity (fringing or resonance) in the curves is caused by phase cancellation and reinforcement due to interaction between the given wavelength and the given particle size.

Figure 2:
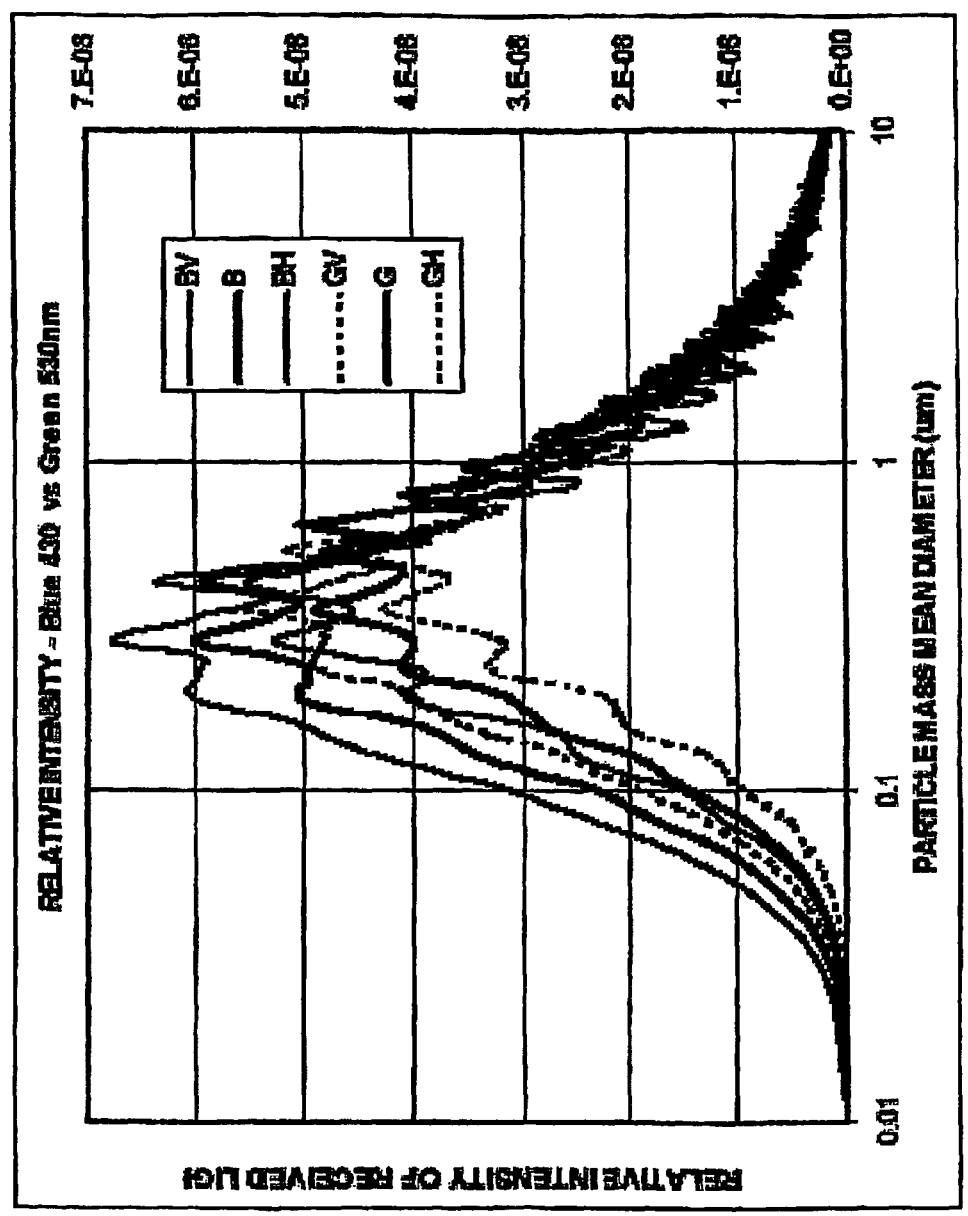
FIG. 2 illustrates results of blue 430 nm and green 530 nm wavelengths to particles over a range of particle sizes.

If instead the combination of wavelengths 430 nm (blue) and 530 nm (green) is examined, the results shown in FIG. 2 are obtained. Here the various graphs are much more similar to each-other and it is difficult to separate the graphs above about 0.5 micron.

The wavelengths chosen to be exemplified have been limited to those of commercially available projectors. Based on the information obtained in FIG. 2 (530 nm), the results for orange (620 nm) would be similar to FIG. 1 (660 nm).

Figure 3:
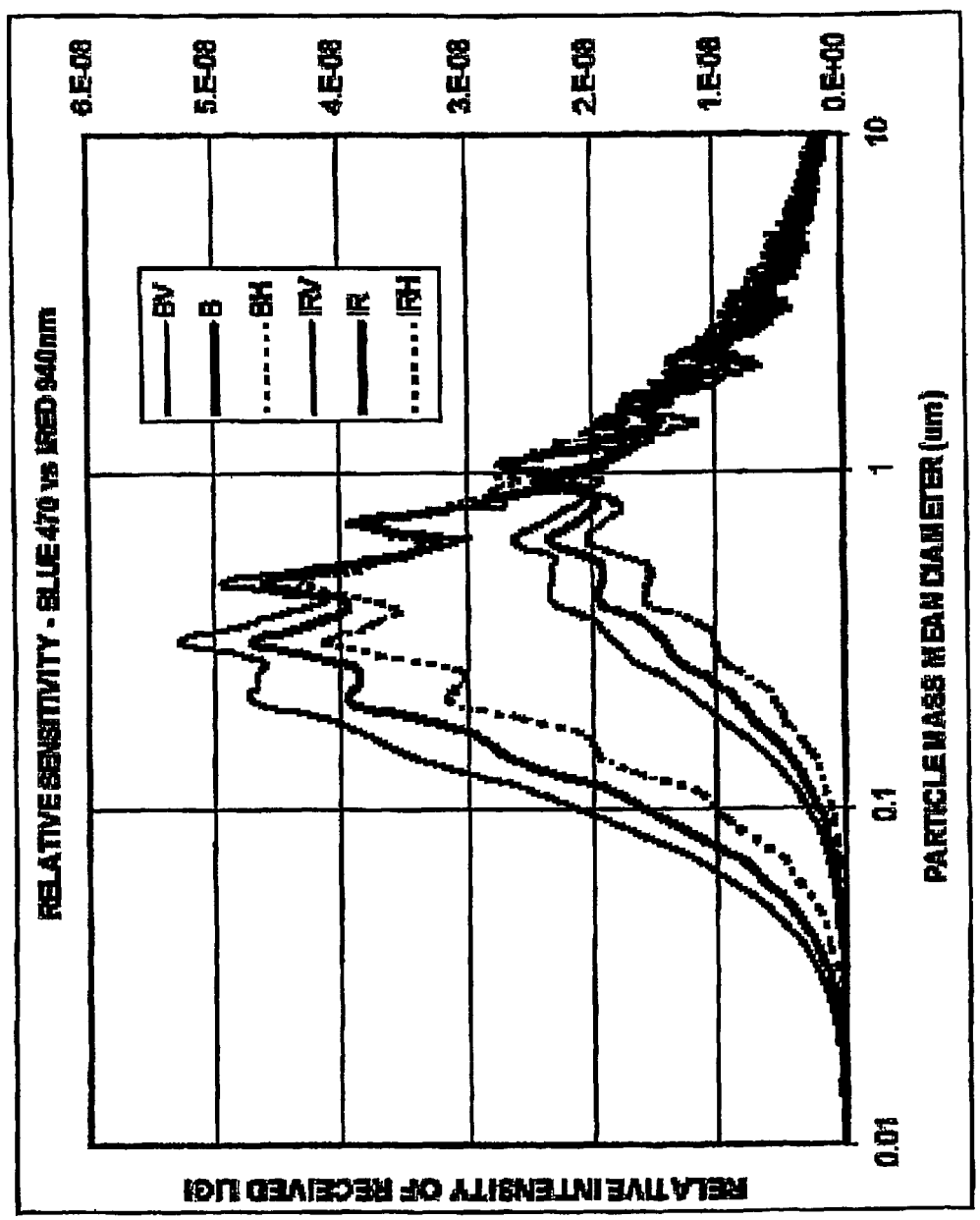
FIG. 3 illustrates results of blue 470 nm and infra-red 940 nm wavelengths to particles over a range of particle sizes.

The results for blue (470 nm) vs infrared (940 nm) are now presented in FIG. 3. In FIG. 3, the wavelength separation is substantially one octave. It can be seen that there is a more clear separation of the graphs in the region below 1 micron, the nominal boundary between smoke and dust.

There would be some merit in operating the monitor at even more-widely separated wavelengths, but currently available technology is a limiting factor. The receiver cell used to detect the scattered light is a PIN photodiode that has enhanced blue response. With a peak response at 850 nm, it's response falls to about 30% at 400 nm and at 1050 nm, so for practical purposes the projector wavelengths are currently limited to this range. Of course, if another receiver cell was able to be used, the wavelengths of light impinging the particles could be altered to have a larger separation.

From the above results, it can be seen that in one embodiment of the present invention, the wavelengths for two projectors for irradiating particles to be detected should preferably lie in the range 400 to 500 nm for blue/violet and 650 to 1050 nm for red/infrared.

In another aspect of the invention, it has been found that if the results of the received signals are compared with each other, such as by comparison of ratio or by being subtracted from each other, that is one signal is subtracted from the other signal, a more reliable 'trigger' or detection signal can be produced indicative of the presence of particles having a size of interest to the application to which the monitor of the present invention is applied. Thus, for example, if the monitor of the present invention is configured as a 'smoke' monitor, then relatively small particles would be of greater interest than larger (dust) particles. Thus, the inventor has realised that for a smoke monitor, for example, blue light has been found to be responsive to relatively small as well as large particle sizes, and that infrared light has been found to be responsive to relatively large particles only. By obtaining a signal which is based on a 'blue' response signal less an 'infrared' response signal, the monitor can be configured to have a relatively higher responsiveness to small particles and a lower or null responsiveness to relatively large particles.

Figure 4:
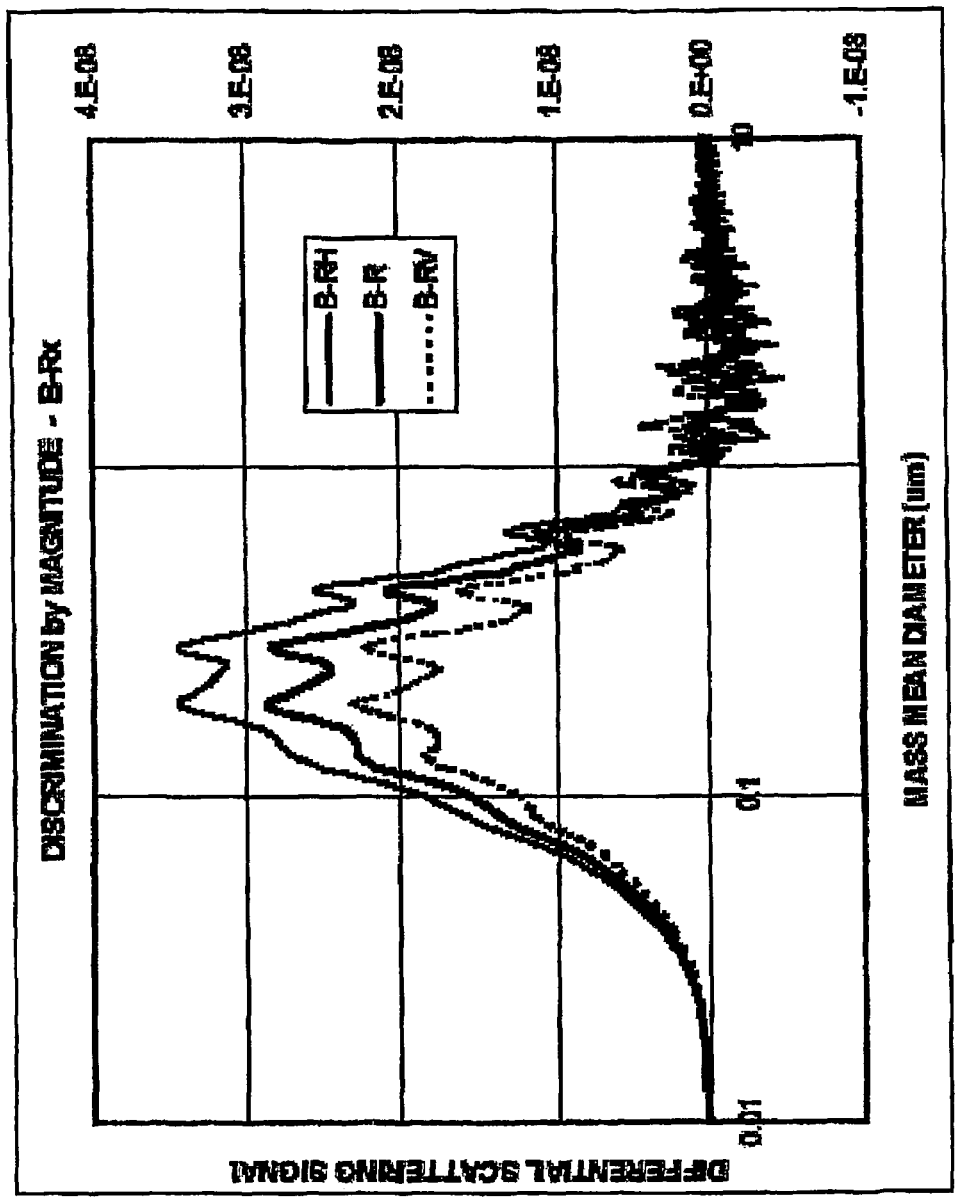
FIG. 4 illustrates the result following the relative subtraction of red from blue signals.

For example, FIG. 4 shows the result of subtracting the red-horizontal (RH), the red unpolarised (R) or the red vertical (RV) from the blue (B) data. A monitor configured in these ways would respond with more sensitivity to particles smaller than one micron, with best sensitivity from the B-RH combination. To avoid clutter the BH and BV results are not shown but they are consistent.

Figure 5:
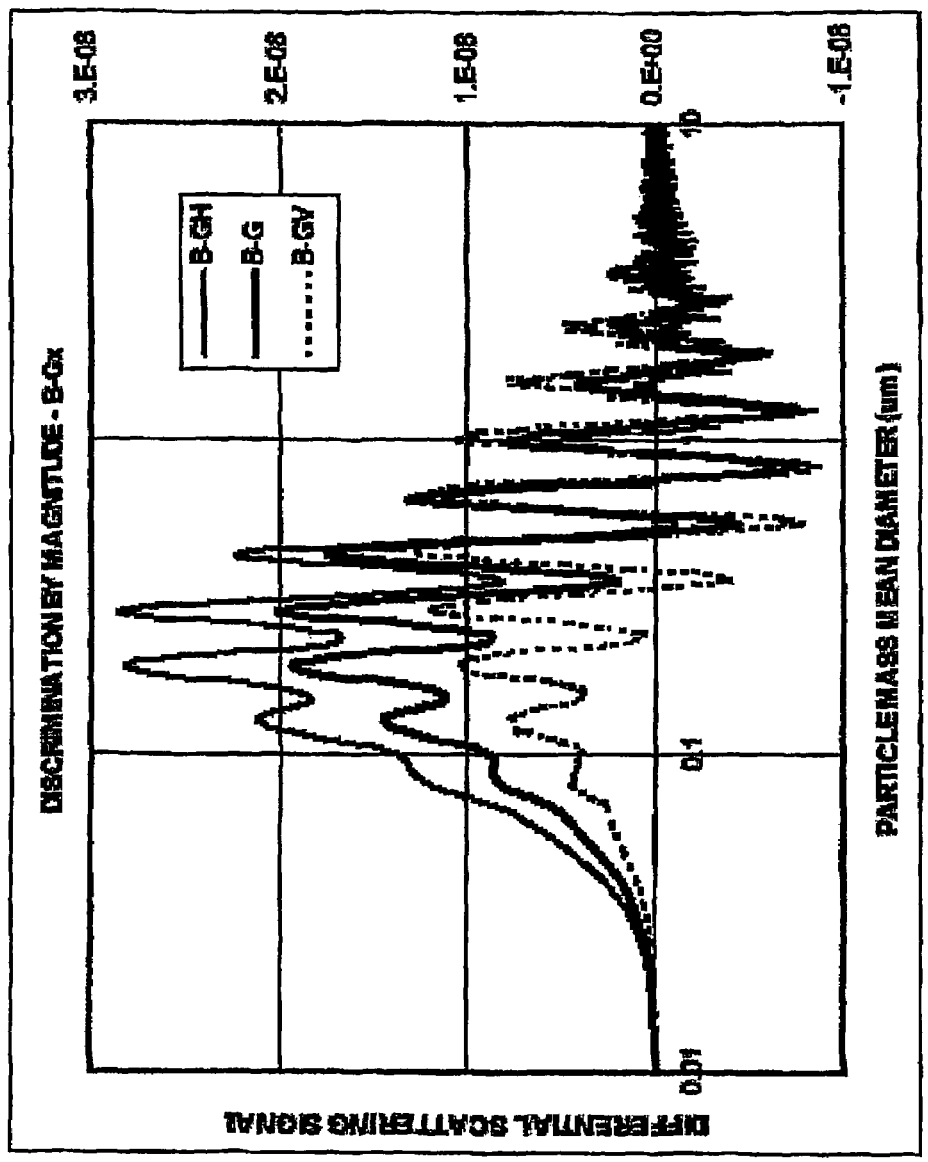
FIG. 5 illustrates the result following the relative subtraction of green from blue signals.

For comparison with FIG. 4, the subtraction of GH, G and GV from B produces the results of FIG. 5. Again, relatively smaller particle sizes are more clearly discernable than larger (dust like) particle sizes although the fringing effects are significant.

Figure 6:
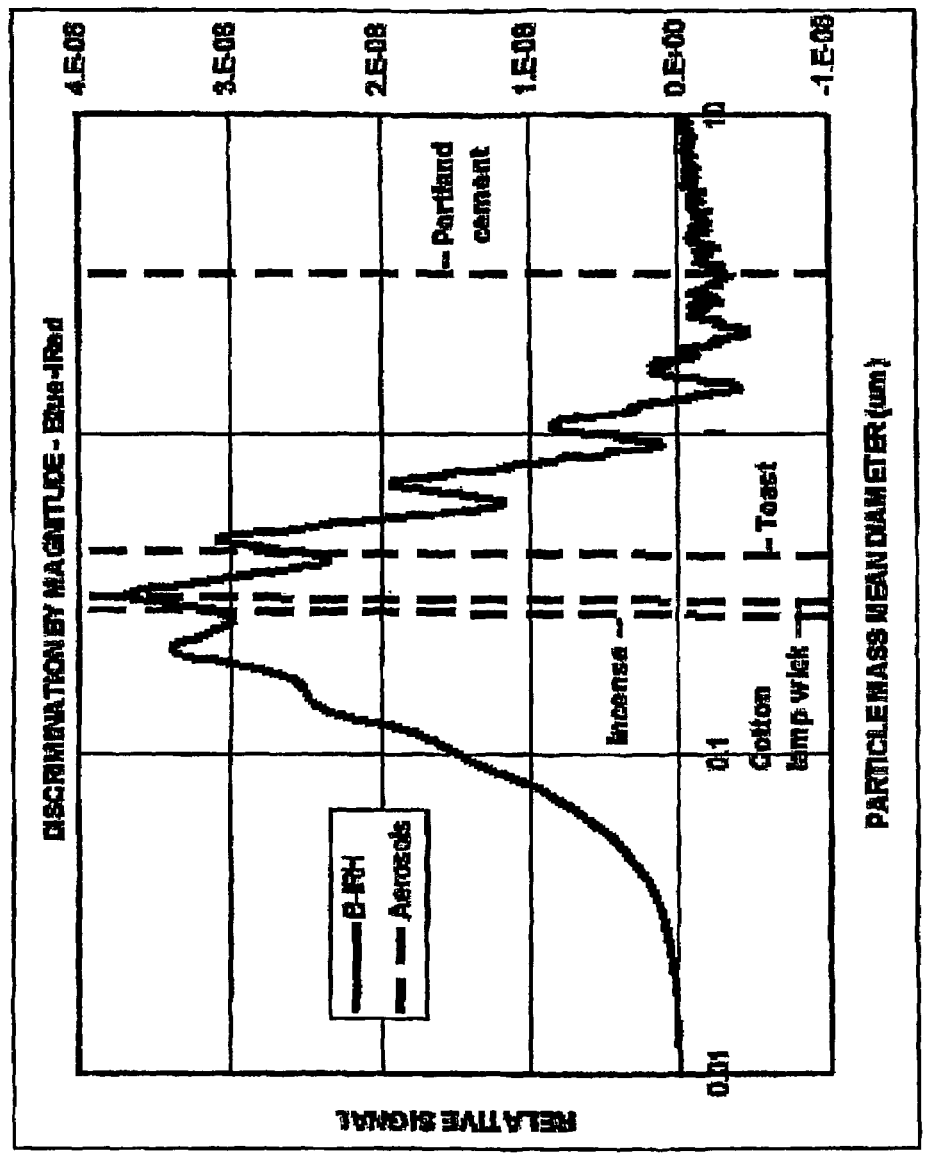
FIG. 6 illustrates the result following the relative subtraction of infrared from blue signals.

FIG. 6 presents the results after subtraction of IRH from B. Other results are omitted for clarity. In addition, some published data on particle mean-sizes obtained for incense, cotton lamp wick, toast and Portland cement (a dust surrogate) are also shown. It can be seen that a monitor configured to perform this subtraction would have appropriate sensitivity to common smoke types while being able to reject (relatively) dust to a significant extent.

Following on from this subtraction aspect, a further aspect of invention has been developed in that an appropriately constructed gain amplifier can be used to provide appropriate output signals for use by alarm or other warning devices or systems. This aspect will be more fully disclosed below. If a third or further wavelength(s) is used in addition to the two wavelengths disclosed above, it will be possible to identify not only small and large particles, but other (intermediate) sized particles, dependent on the wavelength(s) used.

Two Channel Design

Another feature that is provided by the use of a two channel design in accordance with an aspect of invention, is that by subtracting the A (reference) channel from the B (sample) channel (or vise versa) as described herein, we can achieve a null balance. This balance has been found to not significantly vary if the background of the chamber changes with time. The inventor has realised that as the chamber ages or soils over a long time span (a time that is greatly extended by the use of a dust filter), the background light level may change. The benefit of subtracting the channels is that because the response of both channels (especially to dust build-up) is substantially the same, then the effect is self-cancelling, which minimises any change in the resultant output from the adder circuit over time. Note that the signal obtained from dust is not dependent on it being airborne—it can be settled on a surface. The same is true for anything larger than dust—like dust agglomerates or even the walls.

This nulling of drift due to soiling is considered a valuable feature in terms of maintaining calibration.

Signal Level Analysis

Further disclosure of the present invention is made with reference to a smoke monitor application. It is to be noted, however, that the present invention should not be limited to only this application.

Conventional ceiling-mounted "optical" smoke detectors typically provide a sensitivity equivalent to about 10%/m (3%/ft) obscuration, to generate an alarm. The established benchmark for very-high-sensitivity smoke detection requires a sensitivity at least two orders of magnitude higher, equivalent to 0.1%/m obscuration at full-scale with alarm set-points below this level. Eccleston, King & Packham (Eccleston A. J., King N K and Packham D R, 1974: The Scattering Coefficient and Mass Concentration of Smoke from some Australian Forest Fires, APCA Journal, v24 no11) have shown that for eucalypt forest fire smoke, the 0.1%/m level corresponds to a visual range of 4 km and a smoke density of 0.24 mg/m$^3$. Such high sensitivity enables the detection of early stage pyrolysis and thereby provides for the earliest warning of a potential fire in buildings, commensurate with a low rate of false alarms.

Most very-high-sensitivity smoke detectors today utilise an optical chamber with an infrared solid-state laser diode. The long wavelength of infrared light is useful for detecting the relatively large airborne particles characteristic of dust, as well as smoke aerosols from certain types of fires, but comparatively poor at detecting the very small particles evolved in other fires. Conventional solid-state lasers operating at preferably shorter, visible wavelengths would be expensive or could not operate reliably at elevated ambient temperature (60° C.). To overcome these difficulties it was decided to use, in a preferred embodiment of the present invention as applied to smoke monitors, a light-emitting diode (LED) projector operating at the blue and of the visible spectrum (470 nm).

The monitor configuration incorporates this blue projector set at 60° to the receiver cell axis within an optical chamber, as will be further explained below. It also includes a reference projector at 940 nm (infrared) set at the same angle, but horizontally opposed to the blue projector. With an effective projector irradiant cone angle of 10°, the arrangement offers a relatively optimum configuration for maximising system sensitivity while minimising background light that may otherwise swamp the receiver cell.

For the specified smoke density (0.1%/m), comprising particles of (say) 0.3 μm mass median diameter (with a practical, geometric standard deviation of 1.8), Weinert (Weinert D, 2002: Assessment of Light Scattering from Smoke Particles for a Prototype Duct-mounted Smoke Detector, unpublished) has determined that in the monitor configuration used, the signal strength received due to irradiance of this smoke by an unpolarised blue light source, is on the order of 4.5 E−8 per unit irradiance. The Weinert data at 470 nm and 940 nm has been graphed and presented in FIG. 3. Crucially, this means that the "background" light intensity received by the cell, due to unwanted remnant reflections off the chamber walls, must be at least eight orders of magnitude lower than the projector beam intensity, so that the wanted light signal (scattered off smoke) is not swamped.

The blue projector, in one form, is specified to have a luminous intensity of 40 candela (cd) at a drive current of 500 mA. By definition, at 1 cd the power level is 1.464 mW per steradian (sr) so the rated power is 1.464*40=58.6 mW/sr. The 5° half-angle converts to $2\pi(1-\cos(5))=0.024$ sr so the output power is 58.6*0.024=1.4 mW. Incidentally, at this drive current, the projector voltage drop is 4.0V so using a 0.1% duty cycle, the input power to the projector is 0.5*4.0*0.001=2.0 mW which is less than 1% of its maximum power dissipation rating.

Accordingly, at a pulsed projector power output of 1.4 mW, the scattered light signal directed toward the cell is 1.4*4.5 E−8=6.3 E−5 µW for the configuration used. This level of illumination is directed and focused to fall upon the receiver cell, which is a PIN photodiode within the receiver module. The sensitivity of the cell is specified as 0.2 A/W at 400 nm, converting to 0.31 µA/µW at 470 nm. With a specified lens transmission of 92% (uncoated), the signal developed by the illuminated cell is therefore 0.31*6.3 E−5*0.92=1.8 E−5 µA.

The receiver module, in one form, includes a three-stage, AC-coupled pulse preamplifier comprising a current-to-voltage converter followed by two voltage amplifiers. The converter is an operational amplifier with the PIN photodiode connected differentially between the inverting and non-inverting inputs, with negligible series resistance. The feedback resistor may be 3.9M. (shunted by 3.9 pF) so at mid-band frequencies, for an input signal of 1 µA, the output from this stage would be 3.9 E6*1 E−6=3.9 V/µA. In response to the specified cell illumination, the output becomes 3.9*1.8 E−5=7.0 E−5V or 70 µV.

The following two stages, in one form, are operational amplifiers each having a mid-band gain of 10, so the receiver module output should be 7.0 mV at the specified illumination. The calibration full-scale output level for signal processing may be 3V, so the main amplifier voltage-gain would be 3/7.0 E−3=429. Employing two similar stages, this amplifier would require a gain of 21 per stage. In practice a gain of 17 per stage has been found adequate to produce a sensitivity consistent with a nominal 0.1%/m at full scale, as required.

Clearly, the sensitivity of all smoke detectors depends on the particle size and a meaningful standard would require this size (or a range of sizes) to be specified. Nevertheless, the well-established international benchmark of performance is the VESDA Mk3 monitor most recently produced by Vision Systems Australia, using a Xenon light source. In fact this source is comparable with the blue projector, because the spectral characteristic of the Xenon lamp, combined with the spectral response of a PIN photodiode and the light scattering off small aerosol particles or molecules (which favours short wavelengths as $1/\lambda^4$), determine that the characteristic wavelength for calibration of Xenon-based monitors is 470 nm—the same as the blue projector. For this reason, reliable gases such as Nitrogen and FM200 can continue to be used for calibration (which is not possible for infrared laser based detectors).

As stated earlier, the monitor employs two projectors operating at different wavelengths. With reference to FIG. 3, for relatively large particles (>1µ) it is a design objective that the same signal level is generated at the cell by the infrared signal, as is the case for the blue signal. At the infrared wavelength of 940 nm, the receiver cell has a sensitivity of 0.55 µA/µW (compared with 0.31 µA/µW at 470 nm). Since at 940 nm the lens transmission remains 92%, then because all the relevant equations are linear and the geometries are relatively identical, the infrared projector output power can be reduced by a factor of 0.31/0.55=0.56. At a current of 500 mA, the infrared projector has a power level of 343 mW/sr (compared with 58.6 mW/sr for the blue projector), so the required drive current for the infrared projector becomes 500*0.56*58.6/343=48 mA, This drive current would need to be increased if a polarising filter was used, in order to overcome the loss in this filter.

At the required projector drive settings, to a first approximation the small background signal caused by the aggregate reflections off the chamber walls, as seen by the receiver cell, should be at the same (very low) level for either projector. This requires that the reflection (or absorption) of the chamber walls is largely independent of the difference in wavelengths used. Therefore, in the absence of any smoke in the chamber, the differential voltage between the two channel outputs should be approximately zero (or can be so adjusted).

By introducing smoke into the chamber, the voltage on each channel should rise, but the differential voltage between the channels may often be non-zero. This differential voltage provides an indication of the nature of the airborne particles. FIG. 6 indicates the resultant sensitivity when the infrared channel is subtracted from the blue channel. This outcome could be used to highlight the presence of particles smaller than 1µ mass mean diameter. Included in FIG. 6 are lines identifying published data for the mass mean diameter of particles produced from some available materials—Portland cement "dust", toast, cotton lamp wick and incense. The differential voltage should be zero or slightly negative in the first example (large particles), but significantly positive in the other three examples (small particles). This demonstrates the opportunity for discrimination against dust while maintaining good smoke detection.

Figure 7:
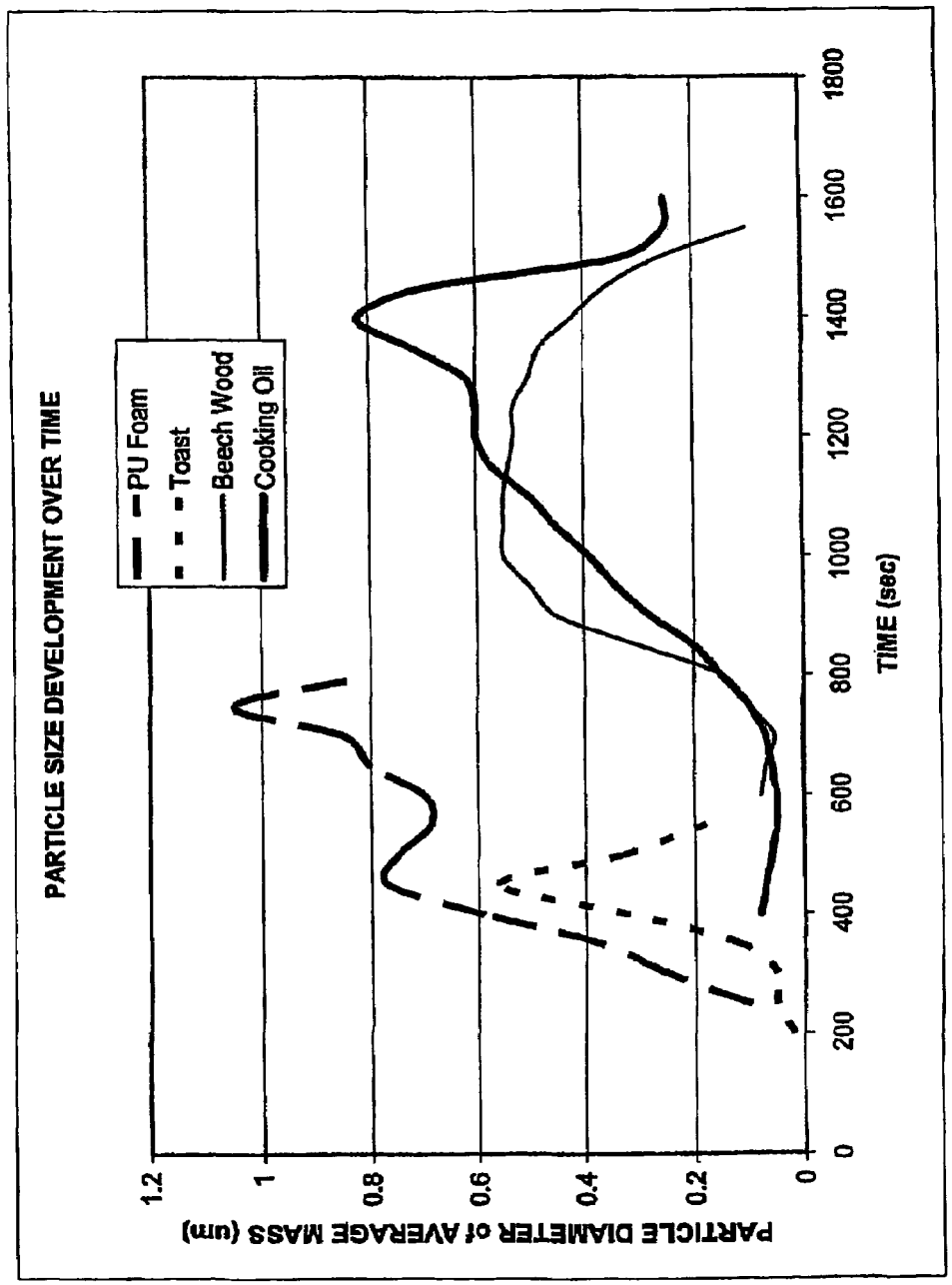
FIG. 7 illustrates the development of particle size over time for various types of fuels.

The particle size in smoke aerosols can vary substantially according to the fuel used, the temperature and period of time, as well as the air flow conditions which determine the oxygen supply, cooling and smoke dilution. In FIG. 7, data from Cleary, Weinert and Mulholland (Cleary T G, Weinert, D W and Mulholland G W, 2001: Moment Method of obtaining Particle Size Measures of Test Smokes, NIST) has been averaged to produce graphs of the aerosol sizes generated by four fuels namely cooking oil (glass dish on hotplate), toast (toaster), polyurethane foam (smouldering) and beech wood blocks (hotplate). It can be seen that in each case the average particle is initially small, increasing in size and then falling as the fuel becomes fully consumed. As a generalisation it can be said that the detection of small particles is important for the earliest possible warning of an incipient fire. Other data shows the aerosol mass concentration peaking in the latter half of each period graphed, and falling at the end.

Figure 8:
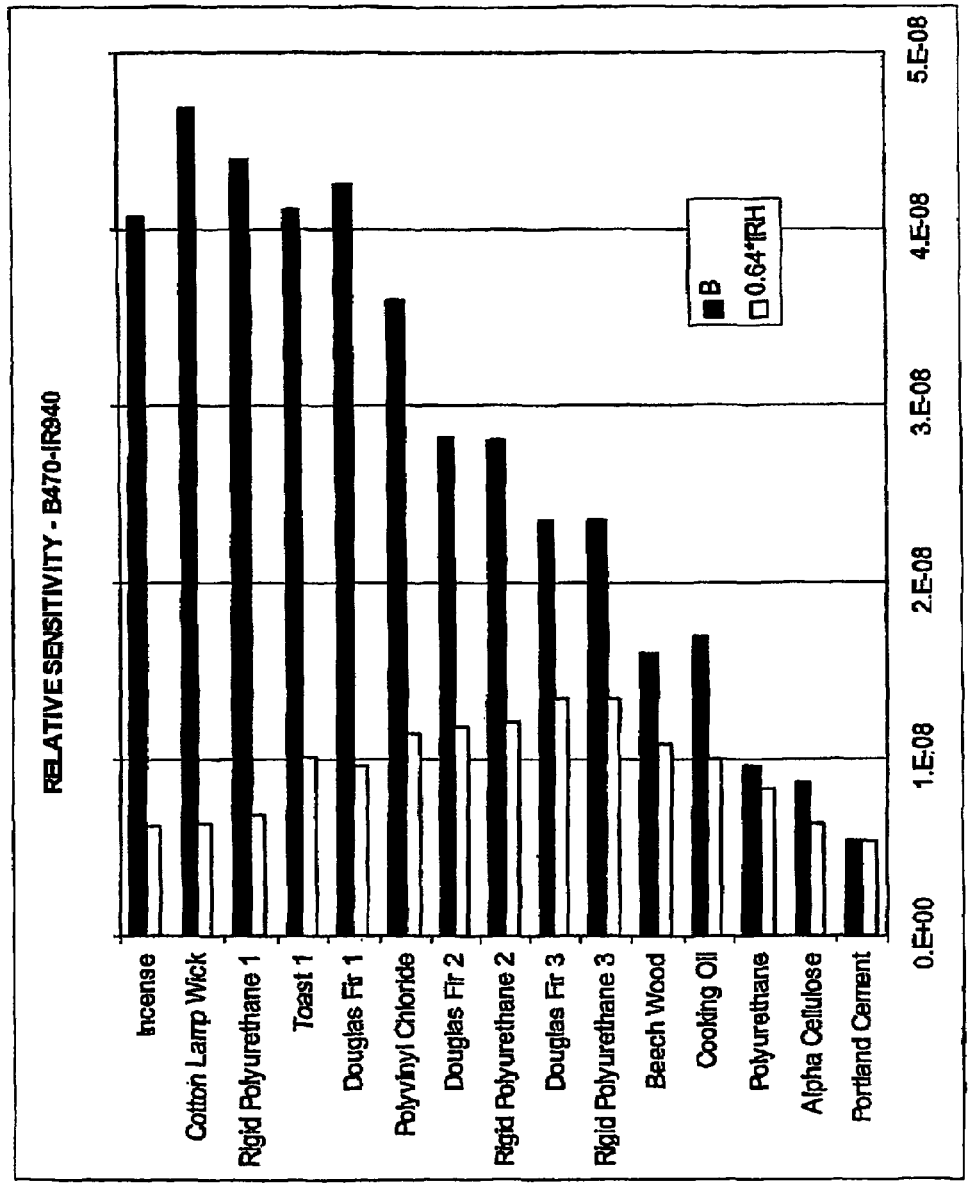
FIG. 8 illustrates a comparative response of infrared and blue channels to smoke from various fuels and/or stages of fire growth.

FIG. 8 provides a more comprehensive comparison of the relative response of the two channels, expected for a number of materials arranged in order of particle size as published. Here the response has been normalised to that of Portland cement (dust surrogate) by reducing the infrared projector signal by a factor of 0.64. Data for Douglas fir and rigid polyurethane (Bankston et al; Bankston C P, Zinn B T, Browner R F and Powell E A, 1981. Aspects of the Mechanisms of Smoke Generation by Burning Materials, Combustion and Flame no 41 pp 273-292) demonstrate the progression of three different stages of radiant heat release rate, which should produce a commensurate differential voltage signature.

To a first approximation and for the reasons stated earlier, FIG. 8 could be regarded as a comparison of expected performance between standard Xenon and current laser based (infrared) detectors.

Moreover, in the case of the two-channel monitor, FIG. 8 demonstrates the opportunity for increased sensitivity compared with these infrared detectors (by up to a factor of four or five), to incipient fire events involving pyrolysis and smouldering, while greatly reducing the sensitivity to false alarms from dust. This could imply that a dust filter is not required. On the contrary, dust filtration is desirable to minimise soiling and thereby to maximise the maintenance period and overall service life of the monitor. Given that a perfect filter for dust would also capture smoke, then the dust discrimination capability can be used to avoid unwanted alarms caused by the small quantity of dust that inevitably passes through a practical filter.

Furthermore, because channel A is predominantly responsive to dust, the output from channel A can be integrated over time (measured in months or years) to record the actual exposure of the chamber and the filter element to dust as distinct from smoke, thereby enabling the service interval to be determined and annunciated in accordance with the (often unpredictable) ambient environment. For example, a service interval may be determined for the dust filter based on accumulating or counting the number of times a dust reading is detected. Once the count reaches or exceeds a predetermined threshold, a service indicator may be illuminated or other wise communicated. Preferably, the service indicator circuit should integrate the actual dust level and the period of its duration.

Logarithmic Output

As noted above, in order to provide a wide output range in sensitivity, prior art detectors provide an analog to digital converter (ADC) used to apply the smoke level data to a microprocessor. With careful design, substantially all of the capacity of the ADC is used to represent the maximum smoke level, such as (typically) 20%/m. ADC's operating at 8-bit resolution are useful, whereas a 10-bit or larger ADC's are more expensive and require larger microprocessors. A 10-bit ADC has been found to allow this 20%/m level to be divided into $2^{10}$=1024 steps, each step representing an increment of 20/1024=0.02%/m. So the steps are 0, 0.02, 0.04, 0.06, etc, with no opportunity for finer increments. At low smoke levels this is considered a very coarse resolution, making it difficult to set alarm thresholds finely. However at high smoke levels, a resolution of 0.02%/m is unnecessary—the ability to set an alarm threshold at 10.00%/m or 10.02%/m for example, has little if any benefit so the resolution of the prior art detectors is considered too coarse at low smoke levels and too fine at high smoke levels.

In accordance with this aspect of invention, however, these prior art disadvantages as noted above are overcome by providing a logarithmic or decile output range. In accordance with the present invention, it has been found that the resolution is appropriate to the given smoke level, namely fine at low smoke levels and coarse at high smoke levels. As an illustration, with the present invention, using a logarithmic output range, at low smoke levels, an alarm threshold could be set at 0.010 or 0.011%/m but with equal ease, at high smoke levels, an alarm threshold could be set at 10%/m or 11%/m.

In other words, realising that smoke is a very variable substance, and there is little benefit in measuring its density (concentration) to an accuracy better than 2 significant figures, the adoption of a logarithmic output provides a beneficial sensitivity resolution over a relatively wide range of smoke levels and/or threshold settings.

Smoke Test Results

A series of trails were conducted using the present invention configured as a smoke monitoring apparatus and constructed and set up in accordance with the Signal Level Analysis disclosure above. The monitor was mounted onto a 200 mm diameter ventilation duct, while a probe was inserted into the duct to sample the air passing through the duct. An inlet fan maintained a relatively continuous flow through the duct, while ensuring that airborne particles were thoroughly mixed with the incoming fresh air. The outlet from the duct was exhausted via a flue. A hotplate operating at approximately 350° C. was positioned at the fan and duct inlet so that small fuel samples could be placed on the hotplate.

The arrangement was such that considerable dilution occurred, because the smoke was entrained and mixed with the predominant flow of fresh air that was continuously drawn into the duct from within the laboratory. This situation was intended to simulate a real protected environment where high levels of dilution would be expected during the early stages of incipient fire growth. Several different fuel samples were separately heated on the hotplate to generate smoke aerosols. In addition, some dust samples were also evaluated without the hotplate by agitating and releasing the dust at the fan and duct inlet.

The output of the two monitor channels A and B were measured to provide the voltage excursion beyond the quiescent (clean air) condition after airborne particles were introduced to the monitor.

Figure 9:
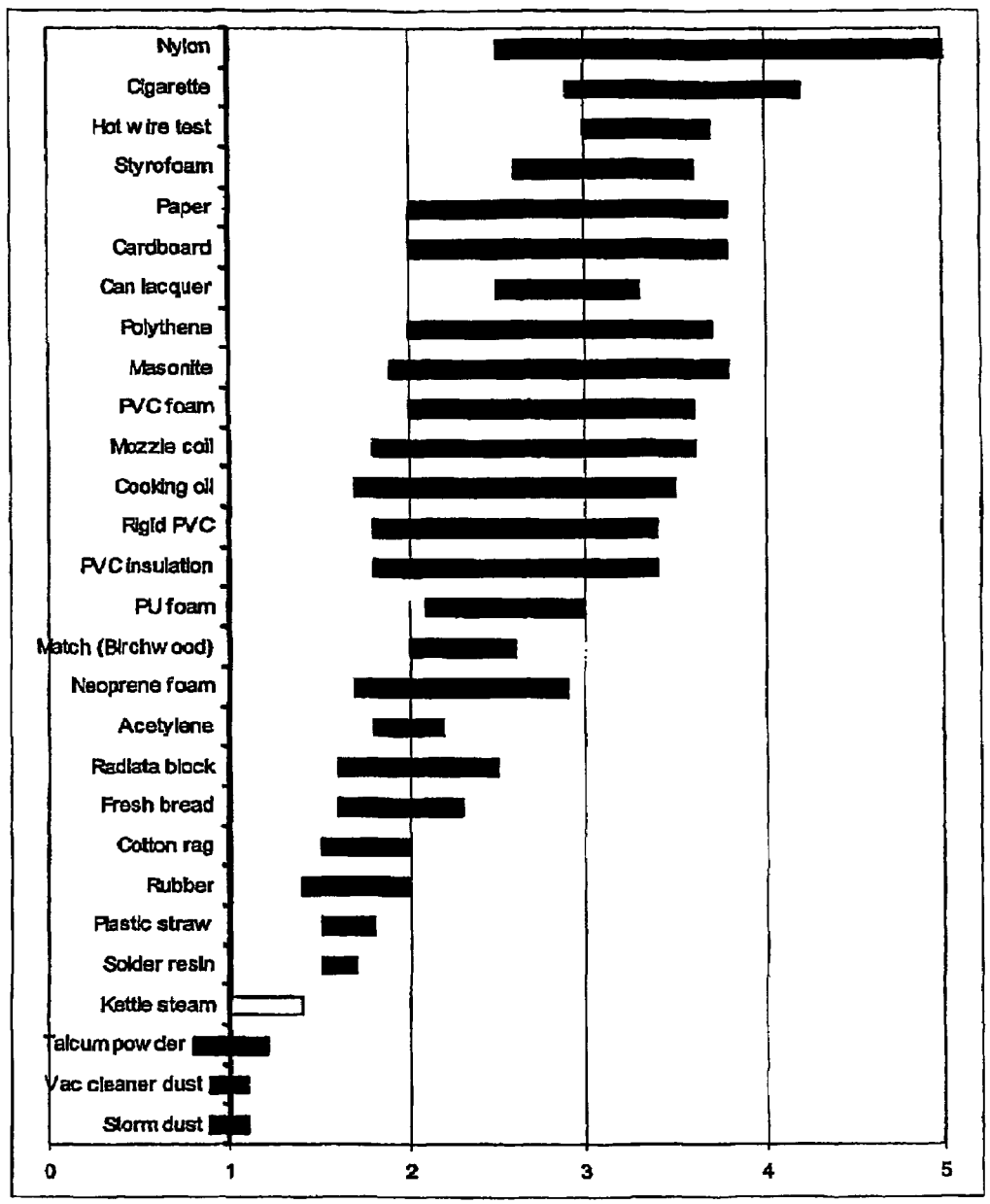
FIG. 9 illustrates relative ratios of channel B and channel A outputs in response to airborne particles from given fuels during a trail.

It was observed that the various fuel types produced smoke aerosols at differing rates and concentrations. As various fuels were heated and consumed, it was expected that the aerosol particle size would vary with time and so the relative output from channels A and B should vary in sympathy. FIG. 9 presents the channel B output expressed as a ratio of the channel A output, in response to a number of particle sources (after making allowance for measurement settling transients). These data are presented as ratios in order to account for the different airborne particle densities involved, given that our current interest is in particle size. The length and position of each horizontal bar represents the range in ratios that occurred during the course of each trail. In many cases the ratio quickly rose to the highest value, then fell slowly. In some cases the ratio rose again after a period at lower values. Some such patterns (signatures) were observed to be distinctly bimodal.

FIG. 9 also represents the relative sensitivity of the monitor to these fuel and dust sources, arranged in apparent order of average particle size. Accordingly, Nylon tubing initially produces the smallest size particles (peak ratio 5.3). After the trial was half completed, the ratio fell slowly, indeed the fuel melts on the hotplate and produces an aerosol for a comparatively long time. Styrene foam has a similar effect. Fuels further down the chart tend to char and produce a solid carbonaceous residue.

The hot wire test consisted of a 2 m length of PVC insulated wire that was heated by passing a high current delivered by a 2V AC "scope" transformer, to simulate an overheating cable that results in early stage pyrolysis.

The result for solder resin comes from the melting of a short length of resin-cored solder and its place in the chart indicates that comparatively large particles (high melting-point droplets) are produced.

The result for steam is anomalous inasmuch as the output readings obtained from a boiling kettle source were of very small magnitude and did not generate an alarm condition, but the ratios involved placed the particle size at the low end of the chart. In contrast, all the other sources produced large output readings and it is only the channel output ratio that is small, in the case of various dust sources (including talcum powder).

Clearly there is a strong differentiation made between smoke aerosols and dust, based upon particle size, so it is possible, with the present embodiment, to discriminate between wanted smoke sources and unwanted dust sources in the process of generating an alarm.

Where the ratio is close to unity, it may be understood that subtraction of channel A (such as infrared) from channel B (such as blue) would result in a greatly reduced reading, such that unwanted alarms from these sources can be avoided. Where the ratio is significantly above unity, subtraction of channel A from channel B would still result in an alarm. Although it is true that the subtraction process could reduce the output of the monitor for certain types of smoke, the fact that unwanted alarms from dust sources can be avoided, permits the monitor to be operated at higher sensitivity than would otherwise be the case.

Furthermore, the results are considered consistent with published data showing that for many fuels, the first particles released by pyrolysis are comparatively small. Therefore, the type of monitor used here can provide the earliest warning of pyrolysis.

Circuit Description

Figure 10:
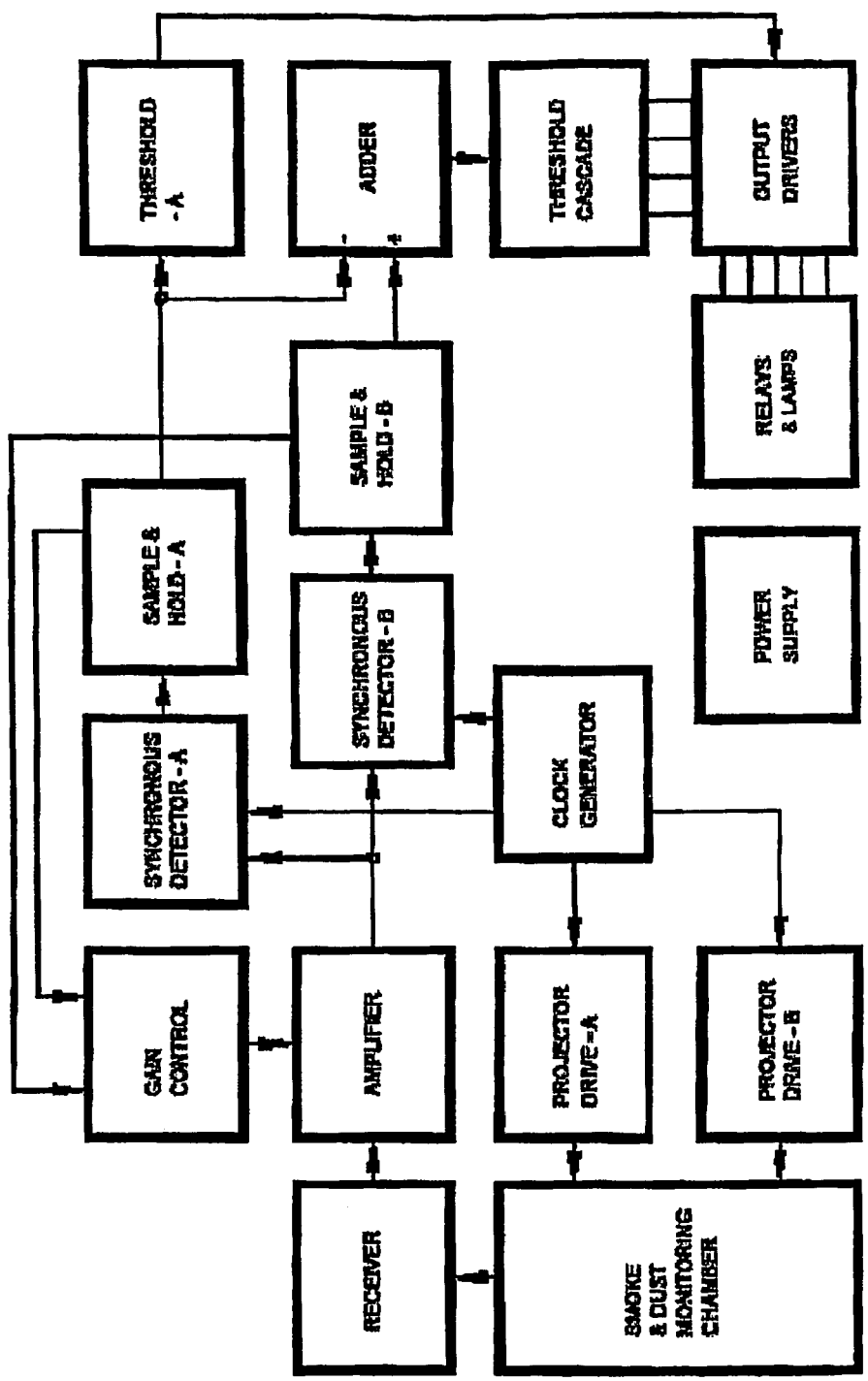
FIG. 10 illustrates a schematic block diagram of a smoke monitor according to one embodiment of the present invention.

FIG. 10 illustrates schematically as a block diagram one form of the present invention useful for detecting smoke. The circuitry drives a pair of light projectors 1 and 2, each projector having different characteristics of wavelength (colour) and/or polarisation. Each projector is driven independently to provide a pulse of light of short duration (for example 0.4 mS), alternately at intervals of (say) 150 mS and 350 mS; This enables an update of the air quality twice per second, being a high sampling refresh rate commensurate with low power consumption.

Some of the light scattered off airborne particles that pass through the monitor chamber 3, is received by a photovoltaic cell (not shown) within a receiver module 4. This signal is amplified in the receiver module 4 and passed to a main amplifier 5 with gain control 6. The amplified signal is then passed to a discriminator (comprising a pair of synchronous detectors 7, 8 and a pair of buffered sample-and-hold circuits 9, 10), which separates the signals derived from the two respective projectors, into two channels, channel A represented by numeral 9 and channel B represented by numeral 10. The two channels provide information about the type of particles in the air. Channel A is particularly responsive to dust particles, while channel B is predominantly sensitive to smoke but has some sensitivity to dust. This is because dust and smoke particles each cover a wide range of sizes, which can overlap to some extent. Therefore in subsequent circuitry, the dust reading of channel A is subtracted from the smoke reading of channel B by virtue of adder 11, resulting in a signal that in essence provides an indication of the smoke density alone.

This smoke density signal is applied to threshold sensing circuitry 12 that operates a series of three lamps and relays 13 in response to the level of fire danger that is detected. These lamps and relays are for example denoted A1 (Alert, or level 1), A2 (Action, or level 2) and A3 (Fire, or level 3). Typically these three alarm levels indicate smoke densities approximately equivalent to 0.03, 0.06 and 0.10%/m obscuration, although the monitor could be calibrated to other settings, and it would be understood that the signals and settings may be configured appropriate to the particular application of the present invention.

In addition, a direct output 14 from the A channel is used to indicate when dust levels are high, independent of the smoke density level. This may also assist in testing, commissioning and demonstrations. This output also indicates when the monitor is in the process of discriminating against dust.

An additional lamp and relay 13 may be configured as a "fail-safe" circuit applied to adder 11, to provide a fault alarm in the event that the monitor is not functioning properly with adequate sensitivity. An analog output from adder 11 may also be provided for remote processing of fault and alarm annunciation. Alternatively, analog outputs may be provided from each of channels A and B to permit remote signature analysis, and processing of fault and alarm annunciation A clock generator 15 may provide appropriate timing signals as is required, and a power supply section 16 may reticulate power to all parts of the circuit at appropriate voltages.

It is necessary that the output signal from the discriminator channels do not saturate when very high levels of smoke or dust are encountered. Such saturation would lose information about the relative signal levels produced by the two projectors, thereby overwhelming the discrimination function. Firstly, the amplifier is provided with a large "headroom" such that full-scale operation is achieved at a signal level (say) half that of saturation. Secondly, an automatic gain control is provided. The DC output voltages from the discriminator channels are fed back to a gain control device to ensure that saturation levels cannot be reached.

Gain Control

Figure 11:
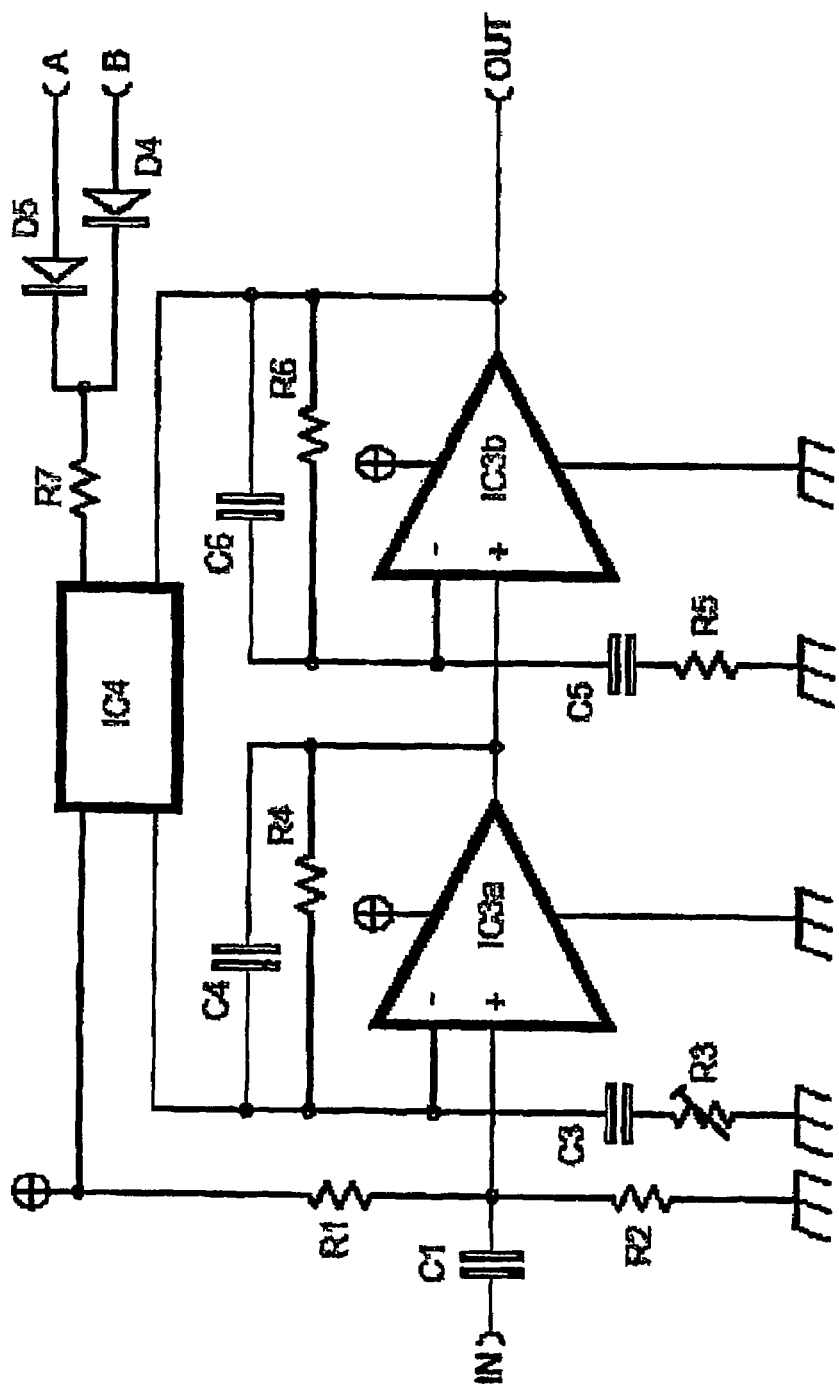
FIG. 11 illustrates a circuit diagram of one form of a gain controlled amplifier according to one embodiment of the present invention.

Referring to FIG. 11, the mid-band gain of an operational amplifier is determined by the ratio of the feedback resistor to the input resistor. In the case of IC3a in FIG. 11, the voltage gain is R4/R3 and in the case of IC3b it is R6/R5. The high frequency breakpoints are determined by C4·R4 and C6·R6, while the low frequency breakpoints are determined by C1· (R1/R2), C3·R3 and C5·R5. The amplifiers are DC coupled and the DC bias is set by R1 and R2.

The gain control device IC4 typically comprises an LDR (light dependent resistor) and an LED (light emitting diode) closely coupled in a light-tight box. The LDR provides an adjustable resistance, the value of which is determined by the current delivered through the LED which is controlled externally by R7. With no current through R7, the LDR resistance is effectively infinite, and at currents of 10 to 20 mA, the resistance falls within the region of 10 kΩ to 100 kΩ. Normally this LDR would be connected across either R4 or R6. This has the disadvantage that in operation, it raises the high frequency breakpoint (either C4·R4 or C6·R6), thereby upsetting the desired frequency response and phase characteristics of the amplifier. Moreover, it has been found that this arrangement produces insufficient dynamic range of gain control.

Because the two-stage circuit is non-inverting to the amplified signal, it is possible to connect the LDR from the output of the second stage (IC3b) to the input of the first stage (IC3a). This greatly increases the effective dynamic range available. Moreover, neither of the breakpoints C4·R4 and C6·R6 is affected when IC4 comes into operation.

The current driving R7 is derived from the sample-and-hold voltage signals (high-going-low) of channel A and channel B, via zener diodes D5 and D6, to ensure that the gain control action does not come into effect until the signal levels are significantly large.

Importantly, the characteristic of the LDR, LED and zener diode combination is neither abrupt nor linear. It is nonlinear, with the effect of providing a logarithmic gain function. An abrupt change in gain could cause instability or erratic behaviour, because a high signal level would cause a sudden reduction in gain, which would cause a sudden reduction in the output, which would in turn reduce the drive to IC4, causing the gain to rise again. In turn, this could cause alarm output relays to chatter. The non-linear design allows for a small increase in output as the input rises to high levels, and provides a wide dynamic range of control.

The normal full-scale sensitivity of the monitor, corresponding to the highest alarm threshold ("fire"), is equivalent to 0.1%/m obscuration, with intermediate alarm thresholds available below this level. By using this logarithmic characteristic it is possible instead to arrange the alarm output thresholds, so that the higher levels of alarm can be in the non-linear region. By this means adequate resolution to provide a first level alarm ("alert") at very low smoke densities such as 0.01%/m can be provided, while the highest level of alarm could be raised to 1% m, 10%/m or even higher.

Chamber Optics

Figure 12:
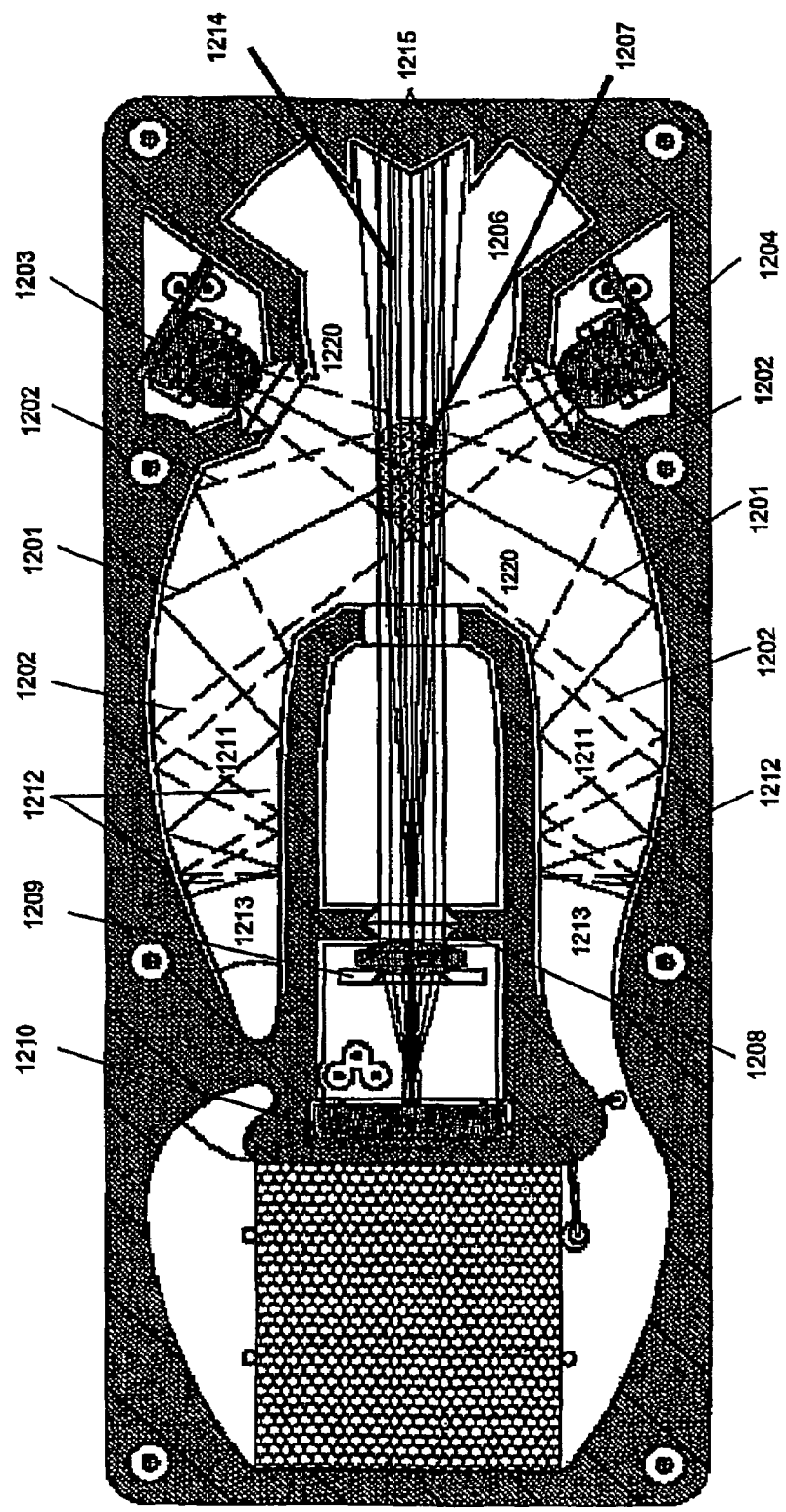
FIGS. 12, 13 illustrate a preferred chamber geometry including indicative light pathways.

FIG. 12 shows the ray diagrams of the projectors, which operate at differing wavelengths and/or polarisations. For clarity, the exemplar rays are shown according to their position at the centre 1201, left or right extremity 1202 of the beam. In practice these beams are operated for a short pulse duration, alternately. It can be seen that the beams are formed by the lensed projector body 1203, 1204 and confined by irises 1205, 1206, so as to pass through the central, monitoring region or zone 1207 of the chamber. If smoke or dust is passing through this zone 1207, a small proportion of the beam energy is scattered off those particles in many directions. Some of this energy is scattered in the direction of a primary receiving iris 1208, and thence to a lens 1209 which focuses the energy onto a photocell within a receiver module 1210. Note that intermediate irises in this pathway have been avoided because stray light reflected off chamber features and thereby coming from inappropriate directions, may reflect off these intermediate irises and into the lens.

Then the direct beams 1201, 1202 pass into an absorbing gallery 1211 where multiple reflections off the highly absorptive walls 1212, dissipate the light energy. The gallery is designed to direct the multiple reflections toward the far end of the gallery 1213, so that many reflections occur before any remnant light could emerge. The combination of this absorption and the geometry of the primary iris in relation to the chamber and the beam irises, avoids swamping the light scattered off smoke or dust particles, by remnants of the originating beams.

The rays 1214 indicate the region made sensitive to the photocell by the receiving lens and primary iris. It can be seen that this sensitive region is focused within the monitoring zone 1207 but the photocell 1210 retains sensitivity along the optical axis beyond the zone. This extended sensitivity is confined by an absorbing region 1215 at the far end of the chamber. The design intent is to ensure that negligible light energy from the projectors 1203, 1204 can fall upon this absorbing region, which would tend to swamp the light scattered off particles. This unwanted light primarily arises from reflections off the projector irises 1205, 1206. A combination of shading this absorbing region, and reflecting stray light away from this area, minimises this swamping light. In addition, the walls of the absorbing region are preferably coloured black to absorb incident light.

Figure 13:
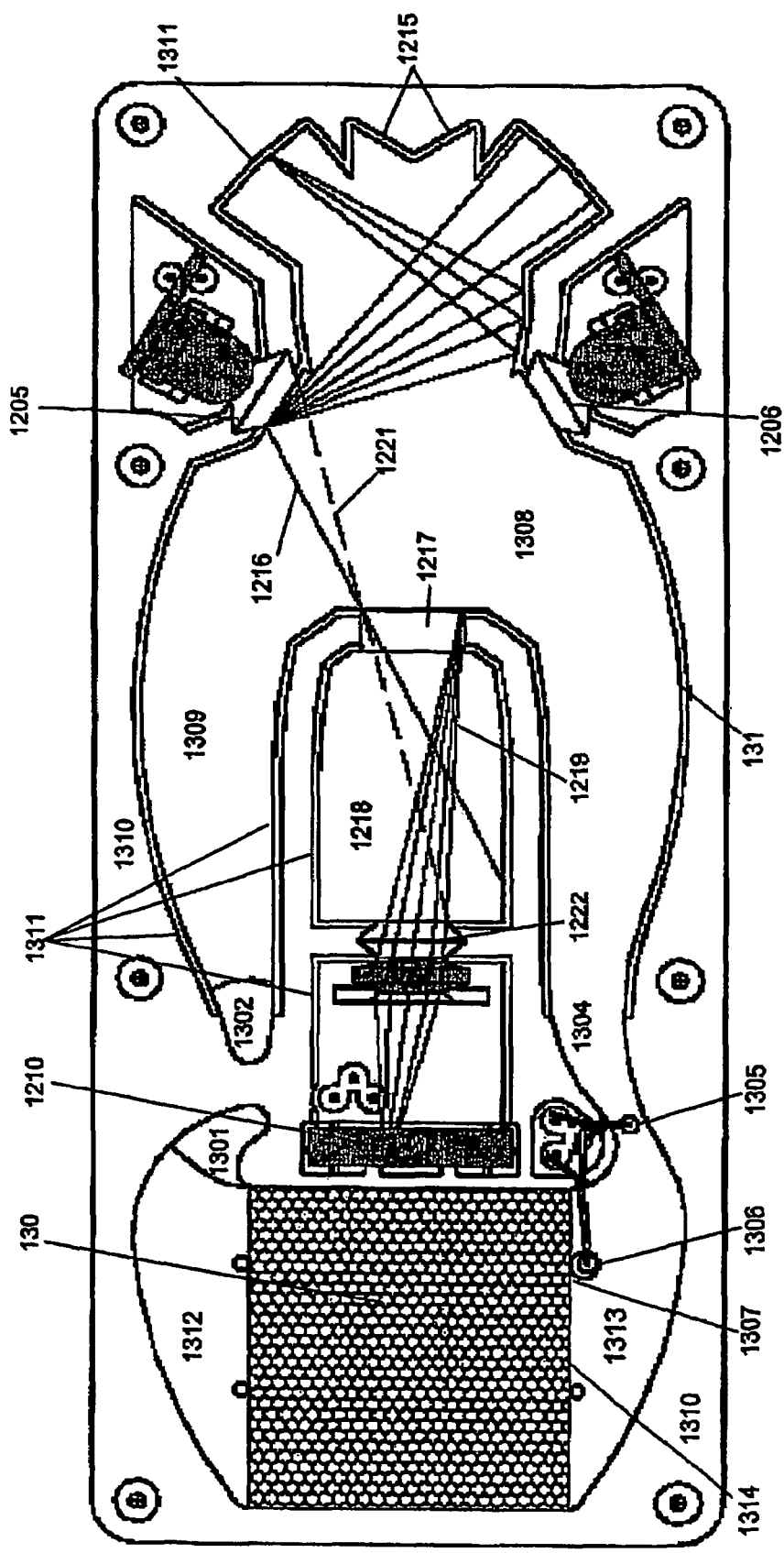

FIG. 13 illustrates typical, unwanted rays arising from reflections off the projector irises 1205, 1206, which are prevented from reaching the central absorbing region 1215. This diagram also includes unwanted rays 1216 that pass through the primary iris 1217 and are absorbed within the receiver gallery 1218. In addition, unwanted rays 1219 that reflect off the primary iris 1217, are shown to focus off-axis from the photocell within the receiver module 1210 and are avoided by means of a photocell iris within the receiver module 1210 (shown as 1401 in FIG. 14).

The combination of all these methods serves to avoid swamping the light scattered off airborne particles. The difficulty of this task can be appreciated from the fact that the scattered light intensity is typically 100 million times lower than the projector light Referring again to FIG. 12, the brightness within the central cone of light 1202 from the projector is regarded as the first order of brightness within the chamber. This bright light is directed towards the absorber gallery 1211, along which it is efficiently absorbed after multiple reflections. Outside of this central cone angle is a second order of brightness 1220 caused by the optics of the projector and reflections off the projector iris. Therefore the whole of the projector iris area must be regarded as bright in many directions. Accordingly the projector iris must be shaded from view by the receiver or lens iris, which is achieved by positioning of the primary iris 1217. To achieve this shading, the chamber geometry is set by a line 1221 (shown dashed in FIG. 13) from the outermost extremity of the projector iris 1205, 1206, to the innermost extremity of the primary iris 1217, to the outermost extremity of the lens iris 1222. This is considered a defining geometry given that an objective of an embodiment of the invention is to produce a monitor of minimum practicable size and the highest possible sensitivity.

Figure 14:
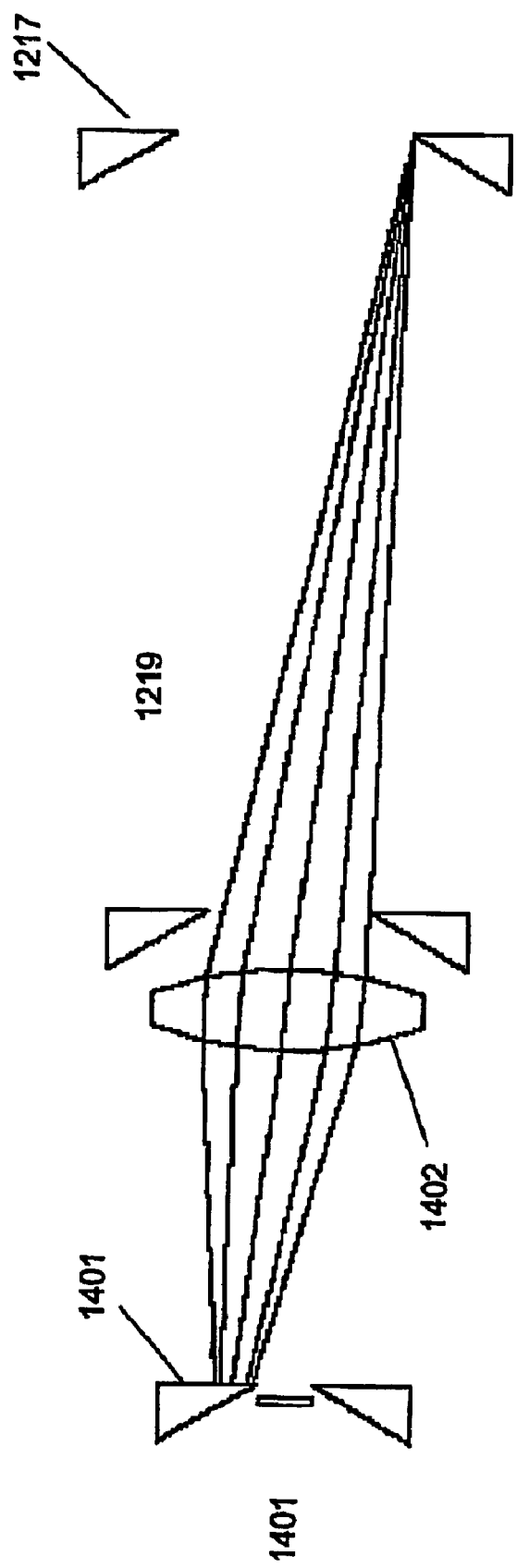
FIG. 14 illustrates the use of a biconvex lens according to an aspect of invention.

Being outside of the central projector cone 1202, the primary iris 1217 is exposed to light of second order brightness 1220 from the projector iris 1203, 1204. Therefore the primary iris 1217 will reflect light of third order brightness 1219, in many directions. Note that in this discussion, an "order of brightness" does not necessarily mean a factor of ten. Given that black surfaces can absorb 99% of the incident light, reflecting only 1% which is yet further reduced by dispersion due to non-specular reflection, then an order of brightness reduction can be a factor of 1000 or more. Accordingly a third order of brightness is not a precise measure, but provides a relative indication. A small proportion of this third order brightness light 1219 will be reflected towards the lens iris 1208 and lens 1209. As shown in FIG. 14, the lens 1209 will focus this unwanted light 1219, off-axis from the receiver cell 1210, to be stopped by the receiver iris 1401. The use of a biconvex lens, a relatively long focal length and a wide primary iris, enable unwanted rays (off-axis) reflected from the primary iris 1217 fall to the side of the receiver cell 1210 and can be attenuated by the receiver iris 1401.

Figure 15:
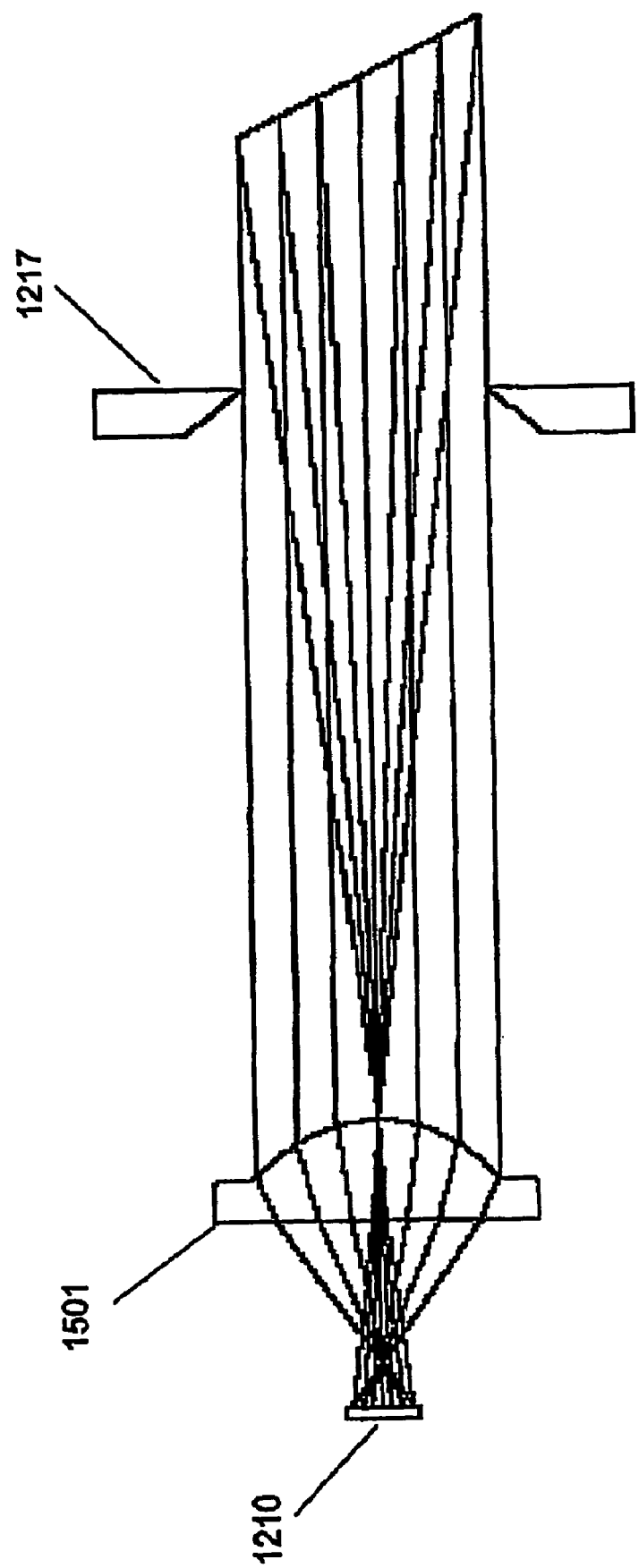
FIG. 15 illustrates the relative operation of an aspheric lens according to an aspect of invention.
Figure 16:
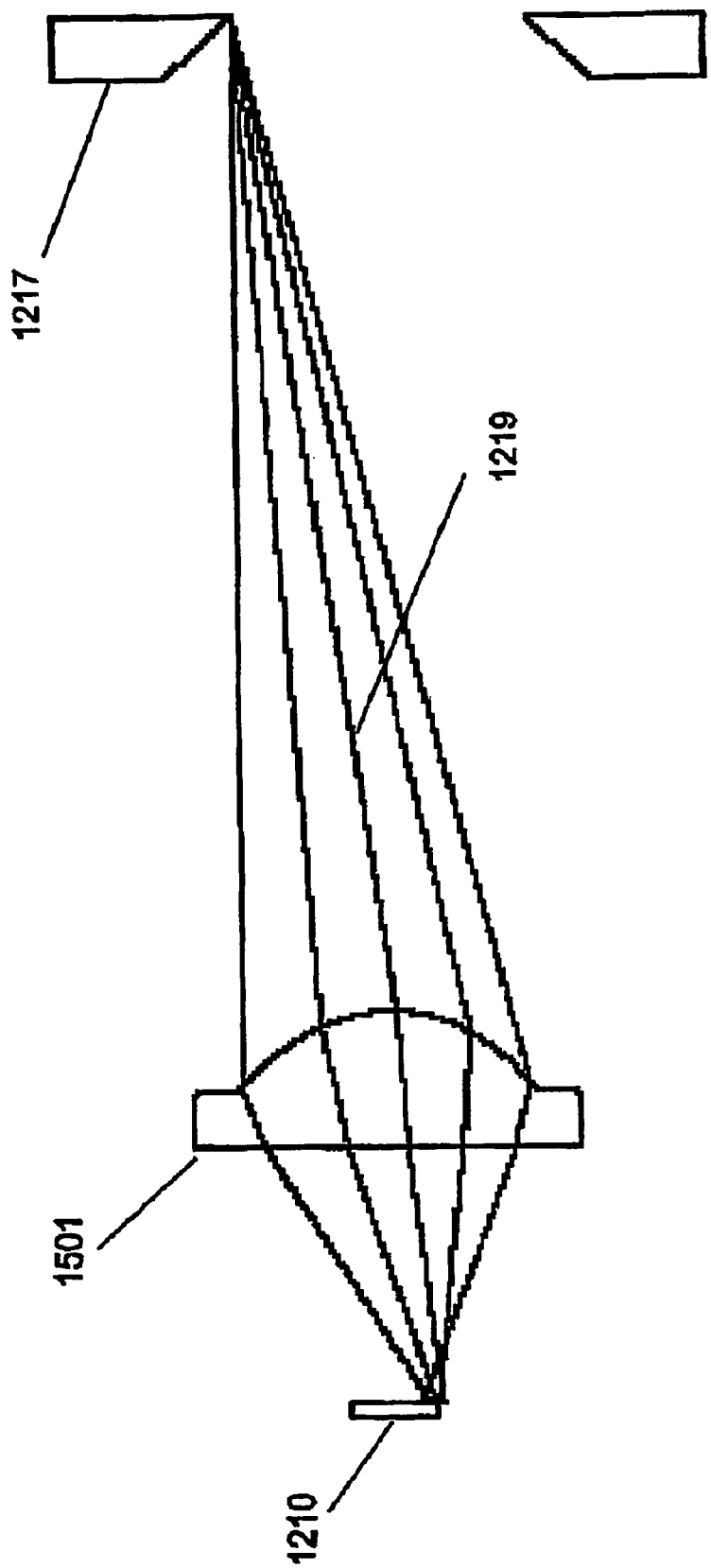
FIG. 16 illustrates the use of an aspheric lens according to an aspect of invention.

It was expected that relatively accurate control of the focusing of the lens was necessary in order to control the separation of the unwanted light from the wanted light. An aspheric lens 1501 (as shown in FIG. 15) of relatively short focal length was proposed. Such a lens provides accurate control of focusing across the whole face of the receiver cell, avoiding spherical aberration and forming an image of photographic quality. FIG. 15 illustrates the operation of such a lens 1501 in focusing scattered light received from particles detected in the monitoring zone 1207 (FIG. 12). FIG. 15 also illustrates the placement of the lens 1501 relative to the primary iris 1217, and the cell 1210. FIG. 16 shows that with such an aspheric lens, however, some of the unwanted light reflected off the primary iris falls upon the cell. This would swamp the wanted signal.

Figure 17:
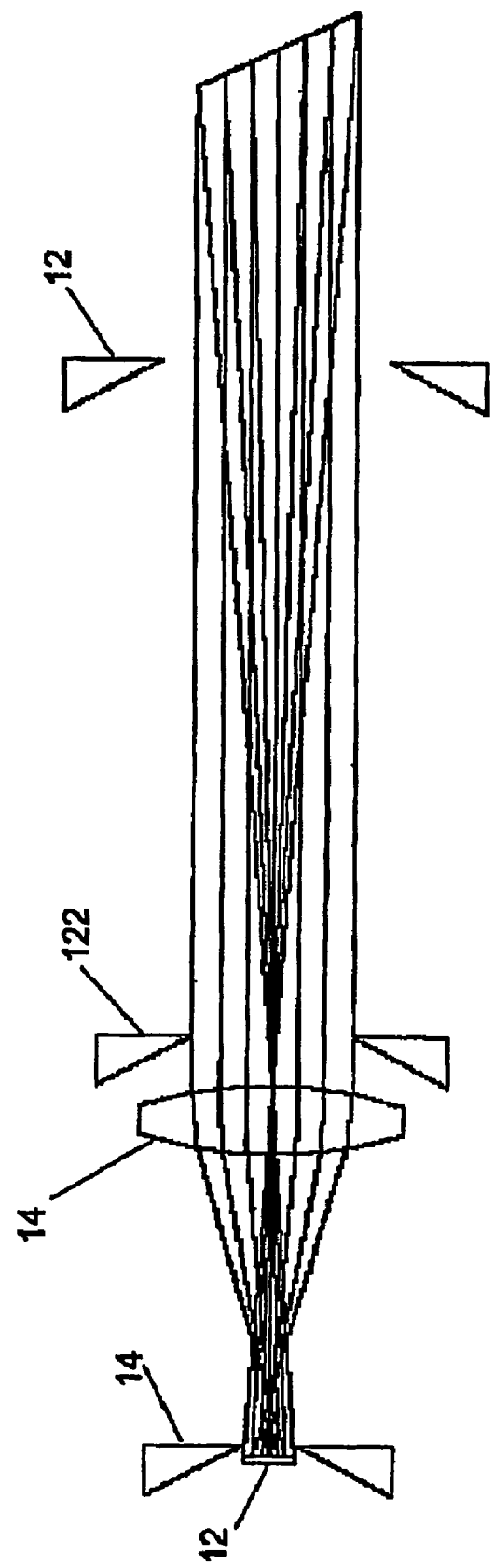
FIG. 17 illustrates the relative operation of a biconvex lens according to an aspect of invention.

Turning again to FIG. 12, a relatively thick biconvex lens (having two convex faces) is used, and which is shown in more detail in FIGS. 14 and 17. As shown in FIG. 14, because the unwanted light 1219 arrives from off-axis directions, the spherical aberration of this type of lens 1402 helps to increase the separation of the two sets of light rays. This separation is further assisted, by using a relatively long focal length (and it has been found that the separation is proportional to focal length). In FIG. 17, it can be seen that the use of the biconvex lens 1402 is made possible because it is not required to form an accurate photographic image at the receiver cell 1210—it is only necessary to collect light, so the point of focus is not so important as the light ray paths involved. In this way, the geometry of the receiver cell 1210 and the lens 1402 is arranged preferably so that a relatively maximum amount of scattered light from detected particles is able to fall onto the receiver cell (as shown in the drawings where the cell 1210 is illuminated with light substantially all over the cell 1210 surface) whilst unwanted light is either blocked from the cell by receiver iris 1401 as described above, or allowed to pass to the side of the cell.

Fluid Dynamics

The design of the chamber from a fluid dynamics standpoint is quite important. One embodiment of the invention includes a miniature duct probe to gather a continuous, small but representative sample of the air passing through a ventilation duct, for example a probe as disclosed in co-pending U.S. patent application 2003/0011770, also by the present inventor.

Referring to FIG. 13, the fluid, such as air, sampled from the environment is drawn into the chamber of the present invention via inlet 1301, passes through the detection chamber and monitoring zone 1207 (FIG. 12) and exits via outlet 1302. It is possible to use a relatively large filter 1303 that can efficiently remove dust for a long period of service, without incurring significant head loss (pressure drop). The preferred type of filter in use is a large-pore, open-cell foam filter of large depth. The smallest dust particles that the filter is designed to remove, are generally at least 10 times smaller than the average pore size of the filter. Dust removal is achieved as a result of Brownian motion (rapid thermal oscillation), by which the dust particles react as if they were many times larger than their physical size. Dust is removed statistically as the flow passes through the deep filter, so that virtually all the dust considered harmful is removed before the flow exits the filter outlet 1314. This has been found to minimise dust build-up (soiling) within the chamber beyond, greatly extending the maintenance period. However, the open structure of the filter avoids a significant problem that has occurred with aspirated smoke detectors of the prior art, namely the removal of smoke particles, increasingly with time, which reduces sensitivity. Moreover, the filter is of a type in which the head loss in the filter does not increase appreciably as the filter becomes loaded with dust.

Typically, smoke particles lie in the range 0.01 to 1 micron, whereas airborne dust particles lie in the range 1 to 100 micron. However there is some overlap at the 1 micron boundary because the smallest dust particles in nature are smaller than the largest possible smoke particles. Therefore it is inappropriate that the filter should be a perfect dust arrestor. To avoid a reduction in sensitivity to smoke, a small fraction of the dust particles must therefore pass through the filter, which needs to be accommodated in other ways (as is disclosed later).

There are mirror-image diffusers, 1312, 1313 either side of the filter 1303. The outlet face 1314 of the filter is presented to a diffuser 1313 that efficiently recombines the flow, turns the flow through 90° and presents the flow to a passage 1304. In a preferred embodiment of the invention, this passage narrows to a cross-sectional area that is still some 5 times larger than the inlet tube, so the loss remains very low, but the local air velocity is some 8 times faster than it is at the exit face 1314 of the filter.

In a preferred embodiment, two sensing devices 1305, 1306 can be mounted, one 1306 at the filter outlet and one 1305 within this narrow region 1304. In this arrangement the sensor 1306 is subject to the relatively very low velocity air flow exiting the filter, so that very little cooling of the sensor takes place. This sensor 1306 may be further protected from cooling by means of a shroud 1307. By contrast, sensor 1305 is relatively fully exposed to a significantly higher velocity air flow and is therefore subject to substantially more cooling than sensor 1306. The two sensors 1305, 1306 are preferably exposed to the same ambient air temperature. Preferably matched devices having a known temperature dependence can be utilised, whereby their different rates of cooling caused by the different air flow velocities to which they are exposed, can be used to generate a different voltage across each sensor, thereby providing a measure of the air velocity in a manner that is largely independent of ambient air temperature.

The sensors may be of the type disclosed in U.S. Pat. No. 4,781,065, however, the positioning of the sensors in the present arrangement of the invention is uniquely different.

Also, in the present arrangement, the sensors are exposed to airflow after it has passed through the dust filter 1303, thus soiling is minimised. Soiling may interfere with the cooling characteristics of the sensors 1305, 1306, thereby detracting from the accuracy of the airflow measurement circuitry.

The flow continues into a further diffuser 1308, which is also the light absorber gallery 1308 for projector 1203 (FIG. 12). As the air flow reaches the mouth of the absorber gallery 1308, a change of direction is imparted while its velocity has slowed to some 25 times less than the velocity at the inlet tube. Therefore very little loss is incurred in the air flow passing through the gallery 1308, across the monitoring zone 1207 (FIG. 12) and into the second gallery 1309. Because the velocity here is relatively low, any remnant dust particles that may be in the air stream, being small in number and size (because of the filter 1303), have a very low momentum and are not therefore spun-out of suspension in the fluid by centrifugal forces, thereby minimising the potential for soiling within the vicinity of the monitoring zone 1207. In the event that there was a tendency for centrifugal separation of dust particles, their direction of momentum would be such that these particles would be deflected harmlessly away from the primary orifice 1217.

The air flow is drawn towards the second absorber gallery 1309 and by diffuser action is gradually and efficiently accelerated and turned to match the exhaust exit 1302. The exhaust air is then efficiently returned to the sampling environment, such as a duct, as described in U.S. Pat. No. 4,781,065 noted above.

It has been explained how the air flow passes through a series of stages in a manner that minimises loss and promotes laminar flow. Accordingly, the chamber is purged with a fresh sample of air very efficiently and quickly, with minimal smoke retention. Despite the low local velocities caused by the large cross-sectional areas, the response of the chamber assembly to changes in smoke levels has proven to be quite rapid, and suitable for the purpose of smoke monitoring alarms.

Because there is very little pressure drop within the monitor of the invention, the absolute pressure anywhere inside the monitor is similar to that inside the duct. Because there can be a large pressure differential between the inside of the duct and the ambient environment in which the monitor is placed, the monitor must maintain a good pressure seal to avoid leakage at any point. The opportunity for leakage is minimised by the chamber design, which comprises two similar halves connected by flat, mating flanges 1310. Therefore only one flat gasket is required to seal the chamber. In one embodiment, a thick closed-cell foam gasket is preferred because this can easily adapt to variations in the chamber flange flatness, overcoming the small amount of bowing and warpage that may occur with plastic injection mouldings. Areas of the chamber, particularly near the monitoring zone 1207, that are sensitive to the light-absorbing quality of the chamber walls, are hidden from the gasket by means of extending small rims 1311 that meet at the centre join of the two chamber halves. Actual contact between the two halves of the chamber is preferred only at these rims, greatly simplifying the demands upon manufacturing of the flatness of mating parts.

The foregoing description has been discussed with the use of a duct probe in mind, however in other embodiment(s) of the invention, the probe may be replaced with other means to capture a sample of the fluid, such as air, to be monitored. This other means (disclosed in U.S. Pat. No. 4,781,065) may be a venturi device within a small-bore pipe such as 20 mm diameter. This pipe may be connected to an aspirating pump or fan (aspirator), placed either upstream or downstream of the venturi. If placed downstream, then a plurality of monitors may be connected to a single aspirator. Upstream of each monitor, the small-bore pipe may extend throughout a fire zone. The sampling pipes may be configured as a network or branches extending into areas or zones where fluid is to be monitored or detected. Each said pipe may contain branches. Each said pipe and branch may contain a number of small holes so that air in the vicinity of each hole is drawn into the pipe. The contribution of air samples from all such holes is then drawn intermittently or relatively continuously towards the venturi. The venturi is designed so that a proportion of the air within the pipe is drawn through the monitor so that the presence of smoke or dust is sensed, before the monitor air flow is returned to the pipe. All the air is then drawn to the aspirator and exhausted.

Note that it is preferred that either in the case of the duct probe or the venturi, only a proportion of the available air passes through the monitor. This proportion or sample of the air contains smoke and/or dust at the same density as the main flow. However, by carefully minimising the flow through the monitor, the rate of dust buildup in the dust filter can be minimised, thereby maximising the maintenance interval without affecting the sensitivity of the monitor.

In a further alternative embodiment of the present invention, instead of the venturi it would be possible to connect the monitor directly to a small-bore tube such as 5 mm internal diameter. This would be suitable for running short distances such as several metres. In this case, the entire air flow would pass through the monitor, but the flow rate would be low and therefore the maintenance interval would not necessarily be affected. To achieve rapid response times with small-bore tubes over long distances the pressure drop would be very high, necessitating an aspirator of high pressure and energy consumption.

Monitor Mounting

Figure 18:
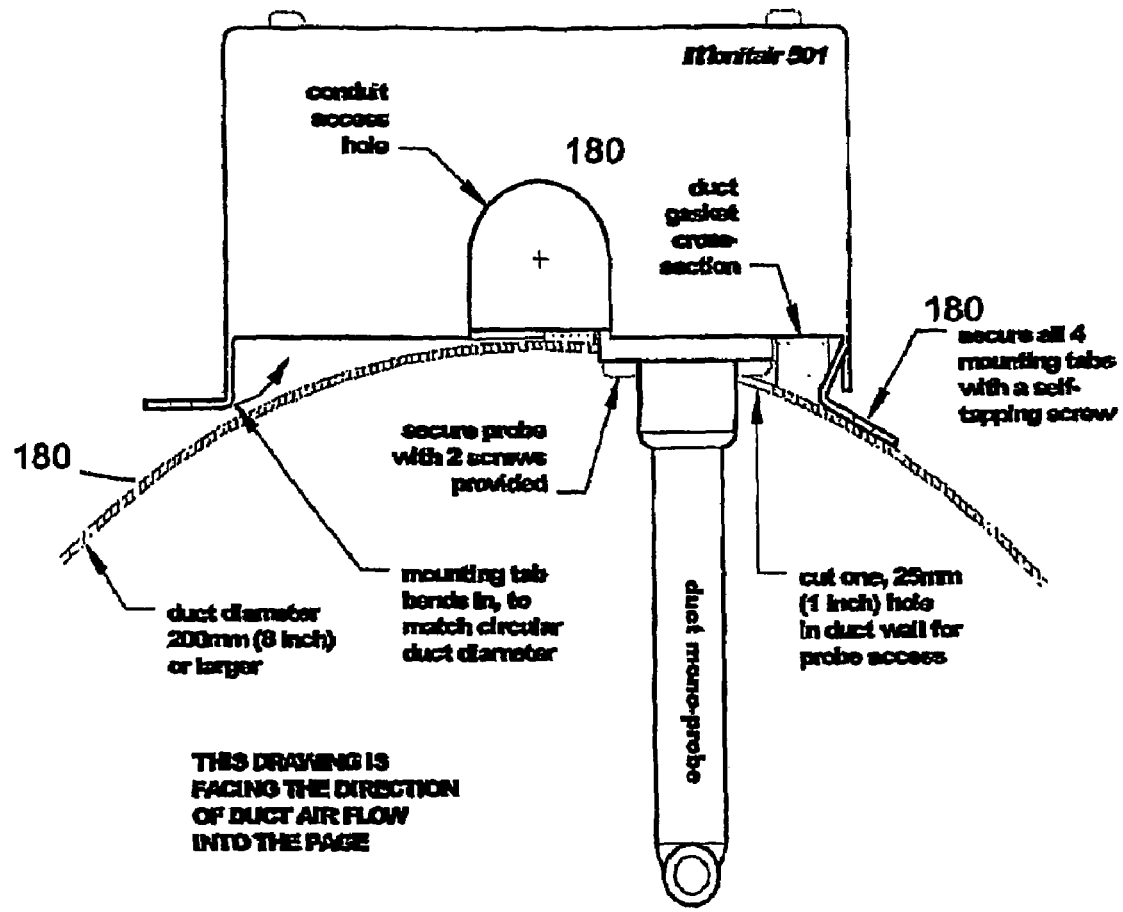
FIG. 18 illustrates an example of the mounting of a detector unit onto a duct arrangement.

Referring to FIG. 18, the monitor 1801, for example a monitor according to the present invention may be mounted to a flat-sided, circular or other shaped surface, such as a duct 1802 by means of mounting tabs 1803. The monitor 1801 may be secured by screws for example, or other suitable means (not shown). In mounting the monitor, the tabs 1803 are simply bent until the tabs match the surface of where the monitor is to be fixed. For example, in mounting to a duct, the tabs are bent till they sit upon or match the surface of the duct, as illustrated in FIG. 18. This duct may be as small as 200 mm (8 inch) diameter. The tabs 1803 may be formed integral with the housing of the monitor 1801, in which case, a slot (not shown) formed in the housing may define the tabs and enable bending of the tabs without skewing, so as to sit firmly on a surface of a duct or other mounting surface.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are. Intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof."

The claims defining the invention are as follows:

1. A method of determining, in a fluid sample, a presence of particles having a substantially predetermined size or a substantially predetermined range of sizes, the method which comprises:
   providing the sample in a chamber;
   illuminating the sample in the chamber with a first wavelength of substantially horizontally and/or vertically polarized light,
   obtaining a first response signal indicative of the first illumination,
   illuminating the sample in the chamber with a second wavelength of light,
   obtaining a second response signal indicative of the second illumination, and
   determining the presence of the particles having the size or range of sizes by subtracting the first signal from the second signal.

2. The method according to claim 1, wherein the second wavelength provides a response signal for particles having the substantially predetermined size or the substantially predetermined range of sizes and for particles not having the substantially predetermined size or the substantially predetermined range of sizes, and the first wavelength provides a response signal for particles not having the substantially predetermined size or outside of the substantially predetermined range of sizes.

3. The method according to claim 1, which further comprises: upon detecting particles of the predetermined size or the range of sizes, triggering an alarm signal.

4. The method according to claim 3, wherein the alarm signal is indicative of an alarm condition for a pyrolysis, smouldering and/or smoke event.

5. The method according to claim 1, which further comprises: providing the first wavelength as infrared light and the second wavelength as blue light.

6. The method according to claim 1, which further comprises: providing the first wavelength of light in the range of 650 nm to 1050 nm, and second wavelength of light is in the range of 400 nm to 500 nm.

7. The method according to claim 1, which further comprises:
illuminating the sample with at least one further wavelength of light, in which particles of at least one further size or range of sizes are relatively responsive to the further wavelength of light, obtaining at least one further response signal indicative of the further illumination, and
determining the presence of the particles of the further size or range of sizes by comparing the first signal, the second signal, and the further signal.

8. The method according to claim 1, which further comprises: polarizing the second illumination.

9. The method according to claim 1, which further comprises: horizontally and/or vertically polarizing the second illumination.

10. The method according to claim 1, which further comprises: providing the first illumination as a relatively longer wavelength that is horizontally polarized and the second illumination as a relatively short wavelength that is vertically polarized.

11. The method according to claim 1, which further comprises: providing the first illumination as a red or infrared light that is horizontally polarized and providing the second illumination as a blue wavelength light that is vertically polarized.

12. The method according to claim 1, which further comprises: providing the first illumination as a red or infrared light that is horizontally polarized and providing the second illumination as a blue light that is un-polarized.

13. A particle monitor adapted to determine, in a fluid sample in a chamber, the presence of particle(s) having a predetermined range of size(s), the monitor comprising:
first illumination means for illuminating the sample in the chamber with a first wavelength of substantially horizontally and/or vertically polarized light, the first light being of a wavelength to which particles of a first size(s) are relatively responsive,
a first signal means for providing a first signal indicative of the first illumination, second illumination means for illuminating the sample in the chamber with a second wavelength of light, the second light being of a wavelength to which particles of a second size(s) are relatively responsive,
a second signal means for providing a second signal indicative of the second illumination, and
logic means for determining the presence of the particles in the predetermined range by subtracting the first signal from the second signal.

14. Apparatus adapted to detect, in a fluid sample in a chamber, particle(s) having a predetermined range of size(s), said apparatus comprising:
processor means adapted to operate in accordance with a predetermined instruction set, said apparatus, in conjunction with said instruction set, being adapted to perform the method comprising the steps of:
illuminating the sample in the chamber with a first wavelength of substantially horizontally and/or vertically polarized light,
obtaining a first response signal indicative of the first illumination,
illuminating the sample in the chamber with a second wavelength of light,
obtaining a second response signal indicative of the second illumination, and determining the presence of the particles having the size or range of size(s) by subtracting the first signal from the second signal.

15. The apparatus according to claim 14, wherein the method further comprises: providing the first wavelength of light as a relatively longer wavelength that is horizontally polarized and the second wavelength of light as a relatively short wavelength that is vertically polarized.

16. The particle monitor according to claim 13, wherein:
the first illumination means provides the first wavelength of light as a relatively longer wavelength that is horizontally polarized; and
the second illumination means provides the second wavelength of light as a relatively short wavelength that is vertically polarized.

* * * * *